US011248217B2

(12) United States Patent
Chundawat et al.

(10) Patent No.: US 11,248,217 B2
(45) Date of Patent: Feb. 15, 2022

(54) ENGINEERED CARBOHYDRATE-ACTIVE ENZYMES FOR GLYCAN POLYMERS SYNTHESIS

(71) Applicant: Rutgers, the State University of New Jersey, New Brunswick, NJ (US)

(72) Inventors: Shishir Chundawat, New Brunswick, NJ (US); Chandra Kanth Bandi, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/545,786

(22) Filed: Aug. 20, 2019

(65) Prior Publication Data

US 2020/0056215 A1 Feb. 20, 2020

Related U.S. Application Data

(60) Provisional application No. 62/719,963, filed on Aug. 20, 2018.

(51) Int. Cl.

| | |
|---|---|
| ***C12N 9/26*** | (2006.01) |
| ***C12N 9/10*** | (2006.01) |
| ***C12P 19/04*** | (2006.01) |
| ***C12N 9/24*** | (2006.01) |

(52) U.S. Cl.

CPC ......... *C12N 9/2402* (2013.01); *C12N 9/1048* (2013.01); *C12P 19/04* (2013.01)

(58) Field of Classification Search

CPC ...... C12N 9/2402; C12N 9/2437; C12P 19/04

See application file for complete search history.

(56) References Cited

U.S. PATENT DOCUMENTS

| | | | | |
|---|---|---|---|---|
| 5,472,859 | A | 12/1995 | Brown et al. | |
| 5,945,314 | A | 8/1999 | Prieto et al. | |
| 9,145,551 | B2 * | 9/2015 | Fox ...................... | C12N 9/2437 |
| 2010/0009902 | A1 | 1/2010 | Defrees | |
| 2013/0137857 | A1 | 5/2013 | Wang | |

FOREIGN PATENT DOCUMENTS

| | | | |
|---|---|---|---|
| WO | 9721822 | A2 | 6/1997 |

OTHER PUBLICATIONS

Studer. Residue mutations and their impact on protein structure and function: detecting beneficial and pathogenic changes. Biochem. J. (2013) 449, 581-594.*

Bandi. Biotechnology and Bioengineering. 2020;117:2944-2956.*

(Continued)

*Primary Examiner* — Yong D Pak

(74) *Attorney, Agent, or Firm* — Saul Ewing Arnstein & Lehr LLP; Domingos J. Silva

(57) ABSTRACT

The present invention relates to engineered carbohydrate-active enzyme constructs that are useful for glycan polymers synthesis. The construct comprises a CD domain from a GH, wherein the domain is conjugated to CBM3a via a peptidic linker. The invention also relates to a method of improving glycan polymer synthesis by using engineered carbohydrate active enzymes comprising a CD domain and CBM3a.

17 Claims, 13 Drawing Sheets

Specification includes a Sequence Listing.

Glycosyl hydrolase (GH)

Carbohydrate Binding Module (CBM)

Linker region

CBM3a

(56) References Cited

OTHER PUBLICATIONS

Bandi, et al., “Engineering a multifunctional family 5 glycosyl hydrolase into a transglycosidase”, American Chemical Society (ACS) Meeting, Boston, MA, Aug. 19-Aug. 23, 2018, Abstract for Presentation, Aug. 19, 2018, 1 page.
Chundawat, “Designer Glycoligands for Enabling Targeted Multimodal Protein Bioseparations”, National Science Foundation Award Abstract #1704679, Aug. 4, 2017, 1 page.
Codera, et al., “Carbohydrate Binding Module assisting glycosynthase-catalyzed polymerizations”, Biochem J, vol. 470, No. 1, Aug. 6, 2015, pp. 15-22.
Light, et al., “Transferase Versus Hydrolase: The Role of Conformational Flexibility in Reaction Specificity”, Structure, vol. 25, Feb. 7, 2017, pp. 295-304.
Maharjan, et al., “Fusion of Carbohydrate Binding Modules to Bifunctional Cellulase to Enhance Binding Affinity and Cellulolytic Activity”, Biotechnology and Bioprocess Engineering, vol. 23, 2018, pp. 79-85.
Mizutani, et al., “Influence of a Mannan Binding Family 32 Carbohydrate Binding Module on the Activity of the Appended Mannanase”, Applied and Environmental Microbiology, vol. 78, No. 14, Jul. 2012, pp. 4781-4787.
Stockinger, et al., “The effect of the carbohydrate binding module on substrate degradation by the human chitotriosidase”. Biochimica et Biophysica Acta (BBA)—Proteins and Proteomics, vol. 1854, Issue 10, Part A, 2015, pp. 1494-1501.

* cited by examiner

CBM3a

| Enzyme | Rate constant (k) (mM/hr) | Error |
|---|---|---|
| CelE-E316G | 0.0014 | 6.64E-05 |
| CelE-CBM3a-E316G | 0.0834 | 8.40E-07 |
| CelE-CBM1-E316G | 0.0054 | 1.84E-04 |
| CelE-E316G-CBM17 | 0.0053 | 1.44E-04 |

1 – pNP-cellobiose
2 – Cellotriose
3 – Cellotetraose
4 – pNP-Glucose
5 – Cellobiose
6 – Glucose

```
SEQUENCE LISTING

<160> NUMBER OF SEQ ID NOS: 30

<210> SEQ ID NO 1
<211> LENGTH: 1377
<212> TYPE: DNA
<213> ORGANISM: Artificial Sequence
<220> FEATURE:
<223> OTHER INFORMATION: Chemically synthesized;  CelE-CBM1

<400> SEQUENCE: 1

atgggacatc accatcatca ccatcaccat gcatccgaaa acctgtactt ccaggcgatc      60

gccatgggaa caaagctttt ggatgcaagc ggaaacgagc ttgtaatgag ggcatgcgt      120

gatatttcag caatagattt ggttaaagaa ataaaaatcg gatggaattt gggaaatact     180

ttggatgctc ctacagagac tgcctgggga aatccaagga caaccaaggc aatgatagaa     240

aaggtaaggg aaatgggctt taatgccgtc agagtgcctg ttacctggga tacacacatc     300

ggacctgctc cggactataa aattgacgaa gcatggctga acagagttga ggaagtggta     360

aactatgttc ttgactgcgg tatgtatgcc atcataaatg ttcaccatga caatacatgg     420

attataccta catatgccaa tgagcaaagg agtaaagaaa aacttgtaaa agtttgggaa     480

caaatagcaa cccgttttaa agattatgac gaccatttgt tgtttgagac aatgaacgaa     540

ccgagagaag taggttcacc tatggaatgg atgggcggaa cgtatgaaaa ccgagatgtg     600

ataaacagat ttaatttggc ggttgttaat accatcagag caagcggcgg aaataacgat     660

aaaagattca tactggttcc gaccaatgcg gcaaccggcc tggatgttgc attaaacgac     720

cttgtcattc cgaacaatga cagcagagta atagtatcca tacatgctta ttcaccgtat     780

ttctttgcta tggatgtcaa cggaacttca tattggggaa gtgactatga caaggcttct     840

tttacaagtg aacttgatgc tatttacaac agatttgtga aaaacggaag ggctgtaatt     900

atcggagaat tcggaaccat tgacaagaac aacctgtctt caagggtggc tcatgccgag     960

cactatgcaa gagaagcagt ttcaagagga attgctgttt tctggtggga taacggctat    1020

tacaatccgg gtgatgcaga aacttatgca ttgctgaaca gaagaaatct tacatggtat    1080

tatcctgaaa ttgtccaggc tcttatgaga ggtgccggcg ttgaaggttt aaacgcgact    1140

cccactaaag gtgccactcc taccaatacg gcgactccga ctaagtcggc aacggcaacg    1200

cccactcgcc ccagcgtacc gaccaatact ccgactaata ccccggcgaa cacccttaag    1260

ccgggtccga cccagagcca ttatggccag tgcggtggta ttggttatag cggtccgacc    1320

gtgtgcgcaa gcggtaccac ctgccaggtg ctgaacccgt attatagcca gtgcctg       1377


<210> SEQ ID NO 2
<211> LENGTH: 459
<212> TYPE: PRT
<213> ORGANISM: Artificial Sequence
<220> FEATURE:
<223> OTHER INFORMATION: Chemically synthesized;  CelE-CBM1

<400> SEQUENCE: 2

Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45
```

-continued

```
Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415

Asn Thr Leu Lys Pro Gly Pro Thr Gln Ser His Tyr Gly Gln Cys Gly
            420                 425                 430

Gly Ile Gly Tyr Ser Gly Pro Thr Val Cys Ala Ser Gly Thr Thr Cys
        435                 440                 445

Gln Val Leu Asn Pro Tyr Tyr Ser Gln Cys Leu
    450                 455
```

<210> SEQ ID NO 3
<211> LENGTH: 1806
<212> TYPE: DNA
<213> ORGANISM: Artificial Sequence
<220> FEATURE:
<223> OTHER INFORMATION: Chemically synthesized; CelE-CBM17

<400> SEQUENCE: 3

```
atgggacatc accatcatca ccatcaccat gcatccgaaa acctgtactt ccaggcgatc     60

gccatgggaa caaagctttt ggatgcaagc ggaaacgagc ttgtaatgag ggcatgcgt     120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccaatact ccgactaata ccccggcgaa cacccttaag   1260

agccaaccga ccgccccgaa agatttttcc tcaggtttct gggactttaa cgatggcacg   1320

acccagggtt tcggcgtgaa tccggactcg ccgattacgg caatcaacgt tgaaaatgct   1380

aacaatgcgc tgaaaattag caacctgaac agcaaaggta gtaacgatct gtccgaaggc   1440

aatttttggg ccaacgtccg catctcagca gacatttggg gtcaatcgat caatatttat   1500

ggcgatacca aactgacgat ggacgtgatc gctccgaccc cggttaacgt cagcattgcg   1560

gccatcccgc agtctagtac gcatggttgg ggcaatccga cccgtgcaat tcgcgtgtgg   1620

acgaacaatt tcgttgctca aaccgatggt acgtataaag cgaccctgac gatctccacc   1680

aacgactcac cgaattttaa caccattgcc accgatgcag ccgactcggt cgttaccaat   1740

atgatcctgt tcgtgggctc caacagcgat aatattagcc tggacaacat caaatttacc   1800

aaataa                                                              1806
```

<210> SEQ ID NO 4
<211> LENGTH: 601
<212> TYPE: PRT
<213> ORGANISM: Artificial Sequence
<220> FEATURE:
<223> OTHER INFORMATION: Chemically synthesized; CelE-CBM17

<400> SEQUENCE: 4

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415
```

```
Asn Thr Leu Lys Ser Gln Pro Thr Ala Pro Lys Asp Phe Ser Ser Gly
            420                 425                 430

Phe Trp Asp Phe Asn Asp Gly Thr Thr Gln Gly Phe Gly Val Asn Pro
        435                 440                 445

Asp Ser Pro Ile Thr Ala Ile Asn Val Glu Asn Ala Asn Asn Ala Leu
    450                 455                 460

Lys Ile Ser Asn Leu Asn Ser Lys Gly Ser Asn Asp Leu Ser Glu Gly
465                 470                 475                 480

Asn Phe Trp Ala Asn Val Arg Ile Ser Ala Asp Ile Trp Gly Gln Ser
                485                 490                 495

Ile Asn Ile Tyr Gly Asp Thr Lys Leu Thr Met Asp Val Ile Ala Pro
            500                 505                 510

Thr Pro Val Asn Val Ser Ile Ala Ala Ile Pro Gln Ser Ser Thr His
        515                 520                 525

Gly Trp Gly Asn Pro Thr Arg Ala Ile Arg Val Trp Thr Asn Asn Phe
    530                 535                 540

Val Ala Gln Thr Asp Gly Thr Tyr Lys Ala Thr Leu Thr Ile Ser Thr
545                 550                 555                 560

Asn Asp Ser Pro Asn Phe Asn Thr Ile Ala Thr Asp Ala Ala Asp Ser
                565                 570                 575

Val Val Thr Asn Met Ile Leu Phe Val Gly Ser Asn Ser Asp Asn Ile
            580                 585                 590

Ser Leu Asp Asn Ile Lys Phe Thr Lys
        595                 600


<210> SEQ ID NO 5
<211> LENGTH: 1734
<212> TYPE: DNA
<213> ORGANISM: Artificial Sequence
<220> FEATURE:
<223> OTHER INFORMATION: Chemically synthesized;  CelE-CBM3a-41aaLinker

<400> SEQUENCE: 5

atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020
```

```
tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccaatact ccgactaata ccccggcgaa caccccagta   1260

agcggtaacc tgaaggttga attttataac tccaacccaa gcgacacaac gaatagcatc   1320

aatccgcagt tcaaagtcac gaacactggc agttcagcta tcgatctgtc gaaactgacc   1380

cttcgttact actatacggt tgatggccaa aaagatcaga ccttttggtg cgaccatgca   1440

gcaatcatcg gtagcaatgg ttcttataac ggcattactt ctaatgtaaa aggcaccttt   1500

gtgaagatgt caagtagcac caacaatgct gatacctacc tggaaattag cttcacgggt   1560

ggcacacttg aaccaggagc ccacgtccag atccagggcc gttttgcgaa aaacgattgg   1620

agcaactata cgcaatcaaa cgattatagt ttcaaaagcg cgtctcaatt cgtagaatgg   1680

gatcaggtga ccgcatattt gaacggagtg ctggtttggg ggaaagaacc agga         1734
```

<210> SEQ ID NO 6
<211> LENGTH: 578
<212> TYPE: PRT
<213> ORGANISM: Artificial Sequence
<220> FEATURE:
<223> OTHER INFORMATION: Chemically synthesized; CelE-CBM3a-41aaLinker

<400> SEQUENCE: 6

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240
```

-continued

```
Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415

Asn Thr Pro Val Ser Gly Asn Leu Lys Val Glu Phe Tyr Asn Ser Asn
            420                 425                 430

Pro Ser Asp Thr Thr Asn Ser Ile Asn Pro Gln Phe Lys Val Thr Asn
        435                 440                 445

Thr Gly Ser Ser Ala Ile Asp Leu Ser Lys Leu Thr Leu Arg Tyr Tyr
    450                 455                 460

Tyr Thr Val Asp Gly Gln Lys Asp Gln Thr Phe Trp Cys Asp His Ala
465                 470                 475                 480

Ala Ile Ile Gly Ser Asn Gly Ser Tyr Asn Gly Ile Thr Ser Asn Val
                485                 490                 495

Lys Gly Thr Phe Val Lys Met Ser Ser Ser Thr Asn Asn Ala Asp Thr
            500                 505                 510

Tyr Leu Glu Ile Ser Phe Thr Gly Gly Thr Leu Glu Pro Gly Ala His
        515                 520                 525

Val Gln Ile Gln Gly Arg Phe Ala Lys Asn Asp Trp Ser Asn Tyr Thr
    530                 535                 540

Gln Ser Asn Asp Tyr Ser Phe Lys Ser Ala Ser Gln Phe Val Glu Trp
545                 550                 555                 560

Asp Gln Val Thr Ala Tyr Leu Asn Gly Val Leu Val Trp Gly Lys Glu
                565                 570                 575

Pro Gly
```

```
<210> SEQ ID NO 7
<211> LENGTH: 1626
<212> TYPE: DNA
<213> ORGANISM: Artificial Sequence
<220> FEATURE:
<223> OTHER INFORMATION: Chemically synthesized;  CelE-CBM3a-6aaLinker

<400> SEQUENCE: 7

atgggacatc accatcatca ccatcaccat gcatccgaaa acctgtactt ccaggcgatc      60

gccatgggaa caaagctttt ggatgcaagc ggaaacgagc ttgtaatgag gggcatgcgt     120
```

```
gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag taagcggtaa cctgaaggtt gaattttata actccaaccc aagcgacaca   1200

acgaatagca tcaatccgca gttcaaagtc acgaacactg gcagttcagc tatcgatctg   1260

tcgaaactga cccttcgtta ctactatacg gttgatggcc aaaaagatca gaccttttgg   1320

tgcgaccatg cagcaatcat cggtagcaat ggttcttata acggcattac ttctaatgta   1380

aaaggcacct ttgtgaagat gtcaagtagc accaacaatg ctgataccta cctggaaatt   1440

agcttcacgg gtggcacact tgaaccagga gcccacgtcc agatccaggg ccgttttgcg   1500

aaaaacgatt ggagcaacta tacgcaatca aacgattata gtttcaaaag cgcgtctcaa   1560

ttcgtagaat gggatcaggt gaccgcatat ttgaacggag tgctggtttg gggaaagaa    1620

ccagga                                                              1626
```

<210> SEQ ID NO 8
<211> LENGTH: 542
<212> TYPE: PRT
<213> ORGANISM: Artificial Sequence
<220> FEATURE:
<223> OTHER INFORMATION: Chemically synthesized; CelE-CBM3a-6aaLinker

<400> SEQUENCE: 8

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95
```

-continued

```
Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Val
    370                 375                 380

Ser Gly Asn Leu Lys Val Glu Phe Tyr Asn Ser Asn Pro Ser Asp Thr
385                 390                 395                 400

Thr Asn Ser Ile Asn Pro Gln Phe Lys Val Thr Asn Thr Gly Ser Ser
                405                 410                 415

Ala Ile Asp Leu Ser Lys Leu Thr Leu Arg Tyr Tyr Tyr Thr Val Asp
            420                 425                 430

Gly Gln Lys Asp Gln Thr Phe Trp Cys Asp His Ala Ala Ile Ile Gly
        435                 440                 445

Ser Asn Gly Ser Tyr Asn Gly Ile Thr Ser Asn Val Lys Gly Thr Phe
    450                 455                 460

Val Lys Met Ser Ser Ser Thr Asn Asn Ala Asp Thr Tyr Leu Glu Ile
465                 470                 475                 480

Ser Phe Thr Gly Gly Thr Leu Glu Pro Gly Ala His Val Gln Ile Gln
                485                 490                 495

Gly Arg Phe Ala Lys Asn Asp Trp Ser Asn Tyr Thr Gln Ser Asn Asp
            500                 505                 510
```

-continued

```
Tyr Ser Phe Lys Ser Ala Ser Gln Phe Val Glu Trp Asp Gln Val Thr
        515                 520                 525

Ala Tyr Leu Asn Gly Val Leu Val Trp Gly Lys Glu Pro Gly
    530                 535                 540


<210> SEQ ID NO 9
<211> LENGTH: 1641
<212> TYPE: DNA
<213> ORGANISM: Artificial Sequence
<220> FEATURE:
<223> OTHER INFORMATION: Chemically synthesized;  CelE-CBM3a-11aaLinker

<400> SEQUENCE: 9

atgggacatc accatcatca ccatcaccat gcatccgaaa acctgtactt ccaggcgatc     60

gccatgggaa caaagctttt ggatgcaagc ggaaacgagc ttgtaatgag gggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccgtaagc ggtaacctga aggttgaatt ttataactcc   1200

aacccaagcg acacaacgaa tagcatcaat ccgcagttca aagtcacgaa cactggcagt   1260

tcagctatcg atctgtcgaa actgaccctt cgttactact atacggttga tggccaaaaa   1320

gatcagacct tttggtgcga ccatgcagca atcatcggta gcaatggttc ttataacggc   1380

attacttcta atgtaaaagg cacctttgtg aagatgtcaa gtagcaccaa caatgctgat   1440

acctacctgg aaattagctt cacgggtggc acacttgaac caggagccca cgtccagatc   1500

cagggccgtt ttgcgaaaaa cgattggagc aactatacgc aatcaaacga ttatagtttc   1560

aaaagcgcgt ctcaattcgt agaatgggat caggtgaccg catatttgaa cggagtgctg   1620

gtttggggga aagaaccagg a                                              1641


<210> SEQ ID NO 10
<211> LENGTH: 547
<212> TYPE: PRT
<213> ORGANISM: Artificial Sequence
<220> FEATURE:
<223> OTHER INFORMATION: Chemically synthesized;  CelE-CBM3a-11aaLinker
```

<400> SEQUENCE: 10

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Val Ser Gly Asn Leu Lys Val Glu Phe Tyr Asn Ser
385                 390                 395                 400
```

```
Asn Pro Ser Asp Thr Thr Asn Ser Ile Asn Pro Gln Phe Lys Val Thr
                405                 410                 415

Asn Thr Gly Ser Ser Ala Ile Asp Leu Ser Lys Leu Thr Leu Arg Tyr
            420                 425                 430

Tyr Tyr Thr Val Asp Gly Gln Lys Asp Gln Thr Phe Trp Cys Asp His
        435                 440                 445

Ala Ala Ile Ile Gly Ser Asn Gly Ser Tyr Asn Gly Ile Thr Ser Asn
    450                 455                 460

Val Lys Gly Thr Phe Val Lys Met Ser Ser Ser Thr Asn Asn Ala Asp
465                 470                 475                 480

Thr Tyr Leu Glu Ile Ser Phe Thr Gly Gly Thr Leu Glu Pro Gly Ala
                485                 490                 495

His Val Gln Ile Gln Gly Arg Phe Ala Lys Asn Asp Trp Ser Asn Tyr
            500                 505                 510

Thr Gln Ser Asn Asp Tyr Ser Phe Lys Ser Ala Ser Gln Phe Val Glu
        515                 520                 525

Trp Asp Gln Val Thr Ala Tyr Leu Asn Gly Val Leu Val Trp Gly Lys
    530                 535                 540

Glu Pro Gly
545
```

<210> SEQ ID NO 11
<211> LENGTH: 1671
<212> TYPE: DNA
<213> ORGANISM: Artificial Sequence
<220> FEATURE:
<223> OTHER INFORMATION: Chemically synthesized; CelE-CBM3a-21aaLinker

<400> SEQUENCE: 11

```
atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140
```

```
cccactaaag gtgccactcc taccaatacg gcgactccga ctaagtcggc aacggtaagc   1200

ggtaacctga aggttgaatt ttataactcc aacccaagcg acacaacgaa tagcatcaat   1260

ccgcagttca aagtcacgaa cactggcagt tcagctatcg atctgtcgaa actgaccctt   1320

cgttactact atacggttga tggccaaaaa gatcagacct tttggtgcga ccatgcagca   1380

atcatcggta gcaatggttc ttataacggc attacttcta atgtaaaagg cacctttgtg   1440

aagatgtcaa gtagcaccaa caatgctgat acctacctgg aaattagctt cacgggtggc   1500

acacttgaac caggagccca cgtccagatc cagggccgtt ttgcgaaaaa cgattggagc   1560

aactatacgc aatcaaacga ttatagtttc aaaagcgcgt ctcaattcgt agaatgggat   1620

caggtgaccg catatttgaa cggagtgctg gtttggggga aagaaccagg a            1671
```

```
<210> SEQ ID NO 12
<211> LENGTH: 557
<212> TYPE: PRT
<213> ORGANISM: Artificial Sequence
<220> FEATURE:
<223> OTHER INFORMATION: Chemically synthesized;  CelE-CBM3a-21aaLinker

<400> SEQUENCE: 12

Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270
```

```
Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Val Ser
385                 390                 395                 400

Gly Asn Leu Lys Val Glu Phe Tyr Asn Ser Asn Pro Ser Asp Thr Thr
                405                 410                 415

Asn Ser Ile Asn Pro Gln Phe Lys Val Thr Asn Thr Gly Ser Ser Ala
            420                 425                 430

Ile Asp Leu Ser Lys Leu Thr Leu Arg Tyr Tyr Tyr Thr Val Asp Gly
        435                 440                 445

Gln Lys Asp Gln Thr Phe Trp Cys Asp His Ala Ala Ile Ile Gly Ser
    450                 455                 460

Asn Gly Ser Tyr Asn Gly Ile Thr Ser Asn Val Lys Gly Thr Phe Val
465                 470                 475                 480

Lys Met Ser Ser Ser Thr Asn Asn Ala Asp Thr Tyr Leu Glu Ile Ser
                485                 490                 495

Phe Thr Gly Gly Thr Leu Glu Pro Gly Ala His Val Gln Ile Gln Gly
            500                 505                 510

Arg Phe Ala Lys Asn Asp Trp Ser Asn Tyr Thr Gln Ser Asn Asp Tyr
        515                 520                 525

Ser Phe Lys Ser Ala Ser Gln Phe Val Glu Trp Asp Gln Val Thr Ala
    530                 535                 540

Tyr Leu Asn Gly Val Leu Val Trp Gly Lys Glu Pro Gly
545                 550                 555


<210> SEQ ID NO 13
<211> LENGTH: 1701
<212> TYPE: DNA
<213> ORGANISM: Artificial Sequence
<220> FEATURE:
<223> OTHER INFORMATION: Chemically synthesized;  CelE-CBM3a-31aaLinker

<400> SEQUENCE: 13

atgggacatc accatcatca ccatcaccat gcatccgaaa acctgtactt ccaggcgatc      60

gccatgggaa caaagctttt ggatgcaagc ggaaacgagc ttgtaatgag gggcatgcgt     120

gatatttcag caatagattt ggttaaagaa ataaaaatcg gatggaattt gggaaatact     180

ttggatgctc ctacagagac tgcctgggga aatccaagga caaccaaggc aatgatagaa     240

aaggtaaggg aaatgggctt taatgccgtc agagtgcctg ttacctggga tacacacatc     300

ggacctgctc cggactataa aattgacgaa gcatggctga acagagttga ggaagtggta     360

aactatgttc ttgactgcgg tatgtatgcc atcataaatg ttcaccatga caatacatgg     420

attataccta catatgccaa tgagcaaagg agtaaagaaa aacttgtaaa agtttgggaa     480
```

```
caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggagaat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccgtaagc ggtaacctga aggttgaatt ttataactcc   1260

aacccaagcg acacaacgaa tagcatcaat ccgcagttca aagtcacgaa cactggcagt   1320

tcagctatcg atctgtcgaa actgaccctt cgttactact atacggttga tggccaaaaa   1380

gatcagacct tttggtgcga ccatgcagca atcatcggta gcaatggttc ttataacggc   1440

attacttcta atgtaaaagg caccctttgtg aagatgtcaa gtagcaccaa caatgctgat   1500

acctacctgg aaattagctt cacgggtggc acacttgaac caggagccca cgtccagatc   1560

cagggccgtt ttgcgaaaaa cgattggagc aactatacgc aatcaaacga ttatagtttc   1620

aaaagcgcgt ctcaattcgt agaatgggat caggtgaccg catatttgaa cggagtgctg   1680

gtttggggga aagaaccagg a                                              1701
```

```
<210> SEQ ID NO 14
<211> LENGTH: 567
<212> TYPE: PRT
<213> ORGANISM: Artificial Sequence
<220> FEATURE:
<223> OTHER INFORMATION: Chemically synthesized;  CelE-CBM3a-31aaLinker

<400> SEQUENCE: 14

Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140
```

-continued

```
Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Glu Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Val Ser Gly Asn Leu Lys Val Glu
                405                 410                 415

Phe Tyr Asn Ser Asn Pro Ser Asp Thr Thr Asn Ser Ile Asn Pro Gln
            420                 425                 430

Phe Lys Val Thr Asn Thr Gly Ser Ser Ala Ile Asp Leu Ser Lys Leu
        435                 440                 445

Thr Leu Arg Tyr Tyr Tyr Thr Val Asp Gly Gln Lys Asp Gln Thr Phe
    450                 455                 460

Trp Cys Asp His Ala Ala Ile Ile Gly Ser Asn Gly Ser Tyr Asn Gly
465                 470                 475                 480

Ile Thr Ser Asn Val Lys Gly Thr Phe Val Lys Met Ser Ser Ser Thr
                485                 490                 495

Asn Asn Ala Asp Thr Tyr Leu Glu Ile Ser Phe Thr Gly Gly Thr Leu
            500                 505                 510

Glu Pro Gly Ala His Val Gln Ile Gln Gly Arg Phe Ala Lys Asn Asp
        515                 520                 525

Trp Ser Asn Tyr Thr Gln Ser Asn Asp Tyr Ser Phe Lys Ser Ala Ser
    530                 535                 540
```

```
Gln Phe Val Glu Trp Asp Gln Val Thr Ala Tyr Leu Asn Gly Val Leu
545                 550                 555                 560

Val Trp Gly Lys Glu Pro Gly
                565


<210> SEQ ID NO 15
<211> LENGTH: 1377
<212> TYPE: DNA
<213> ORGANISM: Artificial Sequence
<220> FEATURE:
<223> OTHER INFORMATION: Chemically synthesized;  CelE-CBM1-E316G

<400> SEQUENCE: 15

atgggacatc accatcatca ccatcaccat gcatccgaaa acctgtactt ccaggcgatc      60

gccatgggaa caaagctttt ggatgcaagc ggaaacgagc ttgtaatgag ggcatgcgt     120

gatatttcag caatagattt ggttaaagaa ataaaaatcg gatggaattt gggaaatact     180

ttggatgctc ctacagagac tgcctgggga aatccaagga caaccaaggc aatgatagaa     240

aaggtaaggg aaatgggctt taatgccgtc agagtgcctg ttacctggga tacacacatc     300

ggacctgctc cggactataa aattgacgaa gcatggctga acagagttga ggaagtggta     360

aactatgttc ttgactgcgg tatgtatgcc atcataaatg ttcaccatga caatacatgg     420

attataccta catatgccaa tgagcaaagg agtaaagaaa aacttgtaaa agtttgggaa     480

caaatagcaa cccgttttaa agattatgac gaccatttgt tgtttgagac aatgaacgaa     540

ccgagagaag taggttcacc tatggaatgg atgggcggaa cgtatgaaaa ccgagatgtg     600

ataaacagat ttaatttggc ggttgttaat accatcagag caagcggcgg aaataacgat     660

aaaagattca tactggttcc gaccaatgcg gcaaccggcc tggatgttgc attaaacgac     720

cttgtcattc cgaacaatga cagcagagta atagtatcca tacatgctta ttcaccgtat     780

ttctttgcta tggatgtcaa cggaacttca tattggggaa gtgactatga caaggcttct     840

tttacaagtg aacttgatgc tatttacaac agatttgtga aaaacggaag ggctgtaatt     900

atcggaggat tcggaaccat tgacaagaac aacctgtctt caagggtggc tcatgccgag     960

cactatgcaa gagaagcagt ttcaagagga attgctgttt tctggtggga taacggctat    1020

tacaatccgg gtgatgcaga aacttatgca ttgctgaaca gaagaaatct tacatggtat    1080

tatcctgaaa ttgtccaggc tcttatgaga ggtgccggcg ttgaaggttt aaacgcgact    1140

cccactaaag gtgccactcc taccaatacg gcgactccga ctaagtcggc aacggcaacg    1200

cccactcgcc ccagcgtacc gaccaatact ccgactaata ccccggcgaa cacccttaag    1260

ccgggtccga cccagagcca ttatggccag tgcggtggta ttggttatag cggtccgacc    1320

gtgtgcgcaa gcggtaccac ctgccaggtg ctgaacccgt attatagcca gtgcctg       1377


<210> SEQ ID NO 16
<211> LENGTH: 459
<212> TYPE: PRT
<213> ORGANISM: Artificial Sequence
<220> FEATURE:
<223> OTHER INFORMATION: Chemically synthesized;  CelE-CBM1-E316G

<400> SEQUENCE: 16

Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30
```

-continued

```
Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415

Asn Thr Leu Lys Pro Gly Pro Thr Gln Ser His Tyr Gly Gln Cys Gly
            420                 425                 430
```

```
Gly Ile Gly Tyr Ser Gly Pro Thr Val Cys Ala Ser Gly Thr Thr Cys
        435                 440                 445

Gln Val Leu Asn Pro Tyr Tyr Ser Gln Cys Leu
    450                 455


<210> SEQ ID NO 17
<211> LENGTH: 1806
<212> TYPE: DNA
<213> ORGANISM: Artificial Sequence
<220> FEATURE:
<223> OTHER INFORMATION: Chemically synthesized;  CelE-CBM17-E316G

<400> SEQUENCE: 17

atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccaatact ccgactaata ccccggcgaa cacccttaag   1260

agccaaccga ccgccccgaa agatttttcc tcaggtttct gggactttaa cgatggcacg   1320

acccagggtt tcggcgtgaa tccggactcg ccgattacgg caatcaacgt tgaaaatgct   1380

aacaatgcgc tgaaaattag caacctgaac agcaaaggta gtaacgatct gtccgaaggc   1440

aatttttggg ccaacgtccg catctcagca gacatttggg gtcaatcgat caatatttat   1500

ggcgatacca aactgacgat ggacgtgatc gctccgaccc cggttaacgt cagcattgcg   1560

gccatcccgc agtctagtac gcatggttgg ggcaatccga cccgtgcaat tcgcgtgtgg   1620

acgaacaatt tcgttgctca aaccgatggt acgtataaag cgaccctgac gatctccacc   1680

aacgactcac cgaattttaa caccattgcc accgatgcag ccgactcggt cgttaccaat   1740

atgatcctgt tcgtgggctc caacagcgat aatattagcc tggacaacat caaatttacc   1800

aaataa                                                              1806
```

```
<210> SEQ ID NO 18
<211> LENGTH: 601
<212> TYPE: PRT
<213> ORGANISM: Artificial Sequence
<220> FEATURE:
<223> OTHER INFORMATION: Chemically synthesized;  CelE-CBM17-E316G

<400> SEQUENCE: 18

Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365
```

```
Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415

Asn Thr Leu Lys Ser Gln Pro Thr Ala Pro Lys Asp Phe Ser Ser Gly
            420                 425                 430

Phe Trp Asp Phe Asn Asp Gly Thr Thr Gln Gly Phe Gly Val Asn Pro
        435                 440                 445

Asp Ser Pro Ile Thr Ala Ile Asn Val Glu Asn Ala Asn Asn Ala Leu
    450                 455                 460

Lys Ile Ser Asn Leu Asn Ser Lys Gly Ser Asn Asp Leu Ser Glu Gly
465                 470                 475                 480

Asn Phe Trp Ala Asn Val Arg Ile Ser Ala Asp Ile Trp Gly Gln Ser
                485                 490                 495

Ile Asn Ile Tyr Gly Asp Thr Lys Leu Thr Met Asp Val Ile Ala Pro
            500                 505                 510

Thr Pro Val Asn Val Ser Ile Ala Ala Ile Pro Gln Ser Ser Thr His
        515                 520                 525

Gly Trp Gly Asn Pro Thr Arg Ala Ile Arg Val Trp Thr Asn Asn Phe
    530                 535                 540

Val Ala Gln Thr Asp Gly Thr Tyr Lys Ala Thr Leu Thr Ile Ser Thr
545                 550                 555                 560

Asn Asp Ser Pro Asn Phe Asn Thr Ile Ala Thr Asp Ala Ala Asp Ser
                565                 570                 575

Val Val Thr Asn Met Ile Leu Phe Val Gly Ser Asn Ser Asp Asn Ile
            580                 585                 590

Ser Leu Asp Asn Ile Lys Phe Thr Lys
        595                 600


<210> SEQ ID NO 19
<211> LENGTH: 1734
<212> TYPE: DNA
<213> ORGANISM: Artificial Sequence
<220> FEATURE:
<223> OTHER INFORMATION: Chemically synthesized;  CelE-CBM3a-E316G-
      41aaLinker

<400> SEQUENCE: 19

atgggacatc accatcatca ccatcaccat gcatccgaaa acctgtactt ccaggcgatc      60

gccatgggaa caaagctttt ggatgcaagc ggaaacgagc ttgtaatgag ggcatgcgt     120

gatatttcag caatagattt ggttaaagaa ataaaaatcg gatggaattt gggaaatact     180

ttggatgctc ctacagagac tgcctgggga aatccaagga caaccaaggc aatgatagaa     240

aaggtaaggg aaatgggctt taatgccgtc agagtgcctg ttacctggga tacacacatc     300

ggacctgctc cggactataa aattgacgaa gcatggctga acagagttga ggaagtggta     360

aactatgttc ttgactgcgg tatgtatgcc atcataaatg ttcaccatga caatacatgg     420

attataccta catatgccaa tgagcaaagg agtaaagaaa aacttgtaaa agtttgggaa     480

caaatagcaa cccgttttaa agattatgac gaccatttgt tgtttgagac aatgaacgaa     540

ccgagagaag taggttcacc tatggaatgg atgggcggaa cgtatgaaaa ccgagatgtg     600

ataaacagat ttaatttggc ggttgttaat accatcagag caagcggcgg aaataacgat     660

aaaagattca tactggttcc gaccaatgcg gcaaccggcc tggatgttgc attaaacgac     720
```

```
cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccaatact ccgactaata ccccggcgaa caccccagta   1260

agcggtaacc tgaaggttga attttataac tccaacccaa gcgacacaac gaatagcatc   1320

aatccgcagt tcaaagtcac gaacactggc agttcagcta tcgatctgtc gaaactgacc   1380

cttcgttact actatacggt tgatggccaa aaagatcaga ccttttggtg cgaccatgca   1440

gcaatcatcg gtagcaatgg ttcttataac ggcattactt ctaatgtaaa aggcaccttt   1500

gtgaagatgt caagtagcac caacaatgct gatacctacc tggaaattag cttcacgggt   1560

ggcacacttg aaccaggagc ccacgtccag atccagggcc gttttgcgaa aaacgattgg   1620

agcaactata cgcaatcaaa cgattatagt ttcaaaagcg cgtctcaatt cgtagaatgg   1680

gatcaggtga ccgcatattt gaacggagtg ctggtttggg ggaaagaacc agga          1734
```

<210> SEQ ID NO 20
<211> LENGTH: 578
<212> TYPE: PRT
<213> ORGANISM: Artificial Sequence
<220> FEATURE:
<223> OTHER INFORMATION: Chemically synthesized; CelE-CBM3a-E316G-41aaLinker

<400> SEQUENCE: 20

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175
```

```
Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Asn Thr Pro Thr Asn Thr Pro Ala
                405                 410                 415

Asn Thr Pro Val Ser Gly Asn Leu Lys Val Glu Phe Tyr Asn Ser Asn
            420                 425                 430

Pro Ser Asp Thr Thr Asn Ser Ile Asn Pro Gln Phe Lys Val Thr Asn
        435                 440                 445

Thr Gly Ser Ser Ala Ile Asp Leu Ser Lys Leu Thr Leu Arg Tyr Tyr
    450                 455                 460

Tyr Thr Val Asp Gly Gln Lys Asp Gln Thr Phe Trp Cys Asp His Ala
465                 470                 475                 480

Ala Ile Ile Gly Ser Asn Gly Ser Tyr Asn Gly Ile Thr Ser Asn Val
                485                 490                 495

Lys Gly Thr Phe Val Lys Met Ser Ser Ser Thr Asn Asn Ala Asp Thr
            500                 505                 510

Tyr Leu Glu Ile Ser Phe Thr Gly Gly Thr Leu Glu Pro Gly Ala His
        515                 520                 525

Val Gln Ile Gln Gly Arg Phe Ala Lys Asn Asp Trp Ser Asn Tyr Thr
    530                 535                 540

Gln Ser Asn Asp Tyr Ser Phe Lys Ser Ala Ser Gln Phe Val Glu Trp
545                 550                 555                 560

Asp Gln Val Thr Ala Tyr Leu Asn Gly Val Leu Val Trp Gly Lys Glu
                565                 570                 575

Pro Gly
```

```
<210> SEQ ID NO 21
<211> LENGTH: 1626
<212> TYPE: DNA
<213> ORGANISM: Artificial Sequence
<220> FEATURE:
<223> OTHER INFORMATION: Chemically synthesized;  CelE-CBM3a-E316G-
      6aaLinker

<400> SEQUENCE: 21

atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag taagcggtaa cctgaaggtt gaattttata actccaaccc aagcgacaca   1200

acgaatagca tcaatccgca gttcaaagtc acgaacactg gcagttcagc tatcgatctg   1260

tcgaaactga cccttcgtta ctactatacg gttgatggcc aaaaagatca gaccttttgg   1320

tgcgaccatg cagcaatcat cggtagcaat ggttcttata acggcattac ttctaatgta   1380

aaaggcacct ttgtgaagat gtcaagtagc accaacaatg ctgataccta cctggaaatt   1440

agcttcacgg gtggcacact tgaaccagga gcccacgtcc agatccaggg ccgttttgcg   1500

aaaaacgatt ggagcaacta tacgcaatca aacgattata gtttcaaaag cgcgtctcaa   1560

ttcgtagaat gggatcaggt gaccgcatat ttgaacggag tgctggtttg ggggaaagaa   1620

ccagga                                                              1626


<210> SEQ ID NO 22
<211> LENGTH: 542
<212> TYPE: PRT
<213> ORGANISM: Artificial Sequence
<220> FEATURE:
<223> OTHER INFORMATION: Chemically synthesized;  CelE-CBM3a-E316G-
      6aaLinker
```

<400> SEQUENCE: 22

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Val
    370                 375                 380

Ser Gly Asn Leu Lys Val Glu Phe Tyr Asn Ser Asn Pro Ser Asp Thr
385                 390                 395                 400

Thr Asn Ser Ile Asn Pro Gln Phe Lys Val Thr Asn Thr Gly Ser Ser
                405                 410                 415
```

```
Ala Ile Asp Leu Ser Lys Leu Thr Leu Arg Tyr Tyr Tyr Thr Val Asp
            420                 425                 430

Gly Gln Lys Asp Gln Thr Phe Trp Cys Asp His Ala Ala Ile Ile Gly
        435                 440                 445

Ser Asn Gly Ser Tyr Asn Gly Ile Thr Ser Asn Val Lys Gly Thr Phe
    450                 455                 460

Val Lys Met Ser Ser Ser Thr Asn Asn Ala Asp Thr Tyr Leu Glu Ile
465                 470                 475                 480

Ser Phe Thr Gly Gly Thr Leu Glu Pro Gly Ala His Val Gln Ile Gln
                485                 490                 495

Gly Arg Phe Ala Lys Asn Asp Trp Ser Asn Tyr Thr Gln Ser Asn Asp
            500                 505                 510

Tyr Ser Phe Lys Ser Ala Ser Gln Phe Val Glu Trp Asp Gln Val Thr
        515                 520                 525

Ala Tyr Leu Asn Gly Val Leu Val Trp Gly Lys Glu Pro Gly
    530                 535                 540


<210> SEQ ID NO 23
<211> LENGTH: 1641
<212> TYPE: DNA
<213> ORGANISM: Artificial Sequence
<220> FEATURE:
<223> OTHER INFORMATION: Chemically synthesized;  CelE-CBM3a-E316G-
      11aaLinker

<400> SEQUENCE: 23

atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccgtaagc ggtaacctga aggttgaatt ttataactcc   1200

aacccaagcg acacaacgaa tagcatcaat ccgcagttca aagtcacgaa cactggcagt   1260

tcagctatcg atctgtcgaa actgaccctt cgttactact atacggttga tggccaaaaa   1320
```

```
gatcagacct tttggtgcga ccatgcagca atcatcggta gcaatggttc ttataacggc   1380

attacttcta atgtaaaagg cacctttgtg aagatgtcaa gtagcaccaa caatgctgat   1440

acctacctgg aaattagctt cacgggtggc acacttgaac caggagccca cgtccagatc   1500

cagggccgtt ttgcgaaaaa cgattggagc aactatacgc aatcaaacga ttatagtttc   1560

aaaagcgcgt ctcaattcgt agaatgggat caggtgaccg catatttgaa cggagtgctg   1620

gtttggggga aagaaccagg a                                              1641
```

<210> SEQ ID NO 24
<211> LENGTH: 547
<212> TYPE: PRT
<213> ORGANISM: Artificial Sequence
<220> FEATURE:
<223> OTHER INFORMATION: Chemically synthesized; CelE-CBM3a-E316G-11aaLinker

<400> SEQUENCE: 24

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300
```

```
Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Val Ser Gly Asn Leu Lys Val Glu Phe Tyr Asn Ser
385                 390                 395                 400

Asn Pro Ser Asp Thr Thr Asn Ser Ile Asn Pro Gln Phe Lys Val Thr
                405                 410                 415

Asn Thr Gly Ser Ser Ala Ile Asp Leu Ser Lys Leu Thr Leu Arg Tyr
            420                 425                 430

Tyr Tyr Thr Val Asp Gly Gln Lys Asp Gln Thr Phe Trp Cys Asp His
        435                 440                 445

Ala Ala Ile Ile Gly Ser Asn Gly Ser Tyr Asn Gly Ile Thr Ser Asn
    450                 455                 460

Val Lys Gly Thr Phe Val Lys Met Ser Ser Ser Thr Asn Asn Ala Asp
465                 470                 475                 480

Thr Tyr Leu Glu Ile Ser Phe Thr Gly Gly Thr Leu Glu Pro Gly Ala
                485                 490                 495

His Val Gln Ile Gln Gly Arg Phe Ala Lys Asn Asp Trp Ser Asn Tyr
            500                 505                 510

Thr Gln Ser Asn Asp Tyr Ser Phe Lys Ser Ala Ser Gln Phe Val Glu
        515                 520                 525

Trp Asp Gln Val Thr Ala Tyr Leu Asn Gly Val Leu Val Trp Gly Lys
    530                 535                 540

Glu Pro Gly
545
```

<210> SEQ ID NO 25
<211> LENGTH: 1671
<212> TYPE: DNA
<213> ORGANISM: Artificial Sequence
<220> FEATURE:
<223> OTHER INFORMATION: Chemically synthesized; CelE-CBM3a-E316G-21aaLinker

<400> SEQUENCE: 25

```
atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600
```

```
ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggtaagc   1200

ggtaacctga aggttgaatt ttataactcc aacccaagcg acacaacgaa tagcatcaat   1260

ccgcagttca aagtcacgaa cactggcagt tcagctatcg atctgtcgaa actgaccctt   1320

cgttactact atacggttga tggccaaaaa gatcagacct tttggtgcga ccatgcagca   1380

atcatcggta gcaatggttc ttataacggc attacttcta atgtaaaagg cacctttgtg   1440

aagatgtcaa gtagcaccaa caatgctgat acctacctgg aaattagctt cacgggtggc   1500

acacttgaac caggagccca cgtccagatc cagggccgtt ttgcgaaaaa cgattggagc   1560

aactatacgc aatcaaacga ttatagtttc aaaagcgcgt ctcaattcgt agaatgggat   1620

caggtgaccg catatttgaa cggagtgctg gtttggggga aagaaccagg a            1671
```

<210> SEQ ID NO 26
<211> LENGTH: 557
<212> TYPE: PRT
<213> ORGANISM: Artificial Sequence
<220> FEATURE:
<223> OTHER INFORMATION: Chemically synthesized; CelE-CBM3a-E316G-21aaLinker

<400> SEQUENCE: 26

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175
```

```
Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Val Ser
385                 390                 395                 400

Gly Asn Leu Lys Val Glu Phe Tyr Asn Ser Asn Pro Ser Asp Thr Thr
                405                 410                 415

Asn Ser Ile Asn Pro Gln Phe Lys Val Thr Asn Thr Gly Ser Ser Ala
            420                 425                 430

Ile Asp Leu Ser Lys Leu Thr Leu Arg Tyr Tyr Tyr Thr Val Asp Gly
        435                 440                 445

Gln Lys Asp Gln Thr Phe Trp Cys Asp His Ala Ala Ile Ile Gly Ser
    450                 455                 460

Asn Gly Ser Tyr Asn Gly Ile Thr Ser Asn Val Lys Gly Thr Phe Val
465                 470                 475                 480

Lys Met Ser Ser Ser Thr Asn Asn Ala Asp Thr Tyr Leu Glu Ile Ser
                485                 490                 495

Phe Thr Gly Gly Thr Leu Glu Pro Gly Ala His Val Gln Ile Gln Gly
            500                 505                 510

Arg Phe Ala Lys Asn Asp Trp Ser Asn Tyr Thr Gln Ser Asn Asp Tyr
        515                 520                 525

Ser Phe Lys Ser Ala Ser Gln Phe Val Glu Trp Asp Gln Val Thr Ala
    530                 535                 540

Tyr Leu Asn Gly Val Leu Val Trp Gly Lys Glu Pro Gly
545                 550                 555
```

<210> SEQ ID NO 27
<211> LENGTH: 1701
<212> TYPE: DNA
<213> ORGANISM: Artificial Sequence

```
<220> FEATURE:
<223> OTHER INFORMATION: Chemically synthesized;  CelE-CBM3a-E316G-
      31aaLinker

<400> SEQUENCE: 27

atgggacatc accatcatca ccatcaccat gcatccgaaa acctgtactt ccaggcgatc     60

gccatgggaa caaagctttt ggatgcaagc ggaaacgagc ttgtaatgag ggcatgcgt    120

gatatttcag caatagattt ggttaaagaa ataaaaatcg gatggaattt gggaaatact    180

ttggatgctc ctacagagac tgcctgggga aatccaagga caaccaaggc aatgatagaa    240

aaggtaaggg aaatgggctt taatgccgtc agagtgcctg ttacctggga tacacacatc    300

ggacctgctc cggactataa aattgacgaa gcatggctga acagagttga ggaagtggta    360

aactatgttc ttgactgcgg tatgtatgcc atcataaatg ttcaccatga caatacatgg    420

attataccta catatgccaa tgagcaaagg agtaaagaaa aacttgtaaa agtttgggaa    480

caaatagcaa cccgttttaa agattatgac gaccatttgt tgtttgagac aatgaacgaa    540

ccgagagaag taggttcacc tatggaatgg atgggcggaa cgtatgaaaa ccgagatgtg    600

ataaacagat ttaatttggc ggttgttaat accatcagag caagcggcgg aaataacgat    660

aaaagattca tactggttcc gaccaatgcg gcaaccggcc tggatgttgc attaaacgac    720

cttgtcattc cgaacaatga cagcagagta atagtatcca tacatgctta ttcaccgtat    780

ttctttgcta tggatgtcaa cggaacttca tattggggaa gtgactatga caaggcttct    840

tttacaagtg aacttgatgc tatttacaac agatttgtga aaaacggaag ggctgtaatt    900

atcggaggat tcggaaccat tgacaagaac aacctgtctt caagggtggc tcatgccgag    960

cactatgcaa gagaagcagt ttcaagagga attgctgttt tctggtggga taacggctat   1020

tacaatccgg gtgatgcaga aacttatgca ttgctgaaca gaagaaatct tacatggtat   1080

tatcctgaaa ttgtccaggc tcttatgaga ggtgccggcg ttgaaggttt aaacgcgact   1140

cccactaaag gtgccactcc taccaatacg gcgactccga ctaagtcggc aacggcaacg   1200

cccactcgcc ccagcgtacc gaccgtaagc ggtaacctga aggttgaatt ttataactcc   1260

aacccaagcg acacaacgaa tagcatcaat ccgcagttca aagtcacgaa cactggcagt   1320

tcagctatcg atctgtcgaa actgaccctt cgttactact atacggttga tggccaaaaa   1380

gatcagacct tttggtgcga ccatgcagca atcatcggta gcaatggttc ttataacggc   1440

attacttcta atgtaaaagg cacctttgtg aagatgtcaa gtagcaccaa caatgctgat   1500

acctacctgg aaattagctt cacgggtggc acacttgaac caggagccca cgtccagatc   1560

cagggccgtt ttgcgaaaaa cgattggagc aactatacgc aatcaaacga ttatagtttc   1620

aaaagcgcgt ctcaattcgt agaatgggat caggtgaccg catatttgaa cggagtgctg   1680

gtttggggga aagaaccagg a                                              1701


<210> SEQ ID NO 28
<211> LENGTH: 567
<212> TYPE: PRT
<213> ORGANISM: Artificial Sequence
<220> FEATURE:
<223> OTHER INFORMATION: Chemically synthesized;  CelE-CBM3a-E316G-
      31aaLinker
```

<400> SEQUENCE: 28

```
Met Gly His His His His His His His His Ala Ser Glu Asn Leu Tyr
1               5                   10                  15

Phe Gln Ala Ile Ala Met Gly Thr Lys Leu Leu Asp Ala Ser Gly Asn
            20                  25                  30

Glu Leu Val Met Arg Gly Met Arg Asp Ile Ser Ala Ile Asp Leu Val
        35                  40                  45

Lys Glu Ile Lys Ile Gly Trp Asn Leu Gly Asn Thr Leu Asp Ala Pro
    50                  55                  60

Thr Glu Thr Ala Trp Gly Asn Pro Arg Thr Thr Lys Ala Met Ile Glu
65                  70                  75                  80

Lys Val Arg Glu Met Gly Phe Asn Ala Val Arg Val Pro Val Thr Trp
                85                  90                  95

Asp Thr His Ile Gly Pro Ala Pro Asp Tyr Lys Ile Asp Glu Ala Trp
            100                 105                 110

Leu Asn Arg Val Glu Glu Val Val Asn Tyr Val Leu Asp Cys Gly Met
        115                 120                 125

Tyr Ala Ile Ile Asn Val His His Asp Asn Thr Trp Ile Ile Pro Thr
    130                 135                 140

Tyr Ala Asn Glu Gln Arg Ser Lys Glu Lys Leu Val Lys Val Trp Glu
145                 150                 155                 160

Gln Ile Ala Thr Arg Phe Lys Asp Tyr Asp Asp His Leu Leu Phe Glu
                165                 170                 175

Thr Met Asn Glu Pro Arg Glu Val Gly Ser Pro Met Glu Trp Met Gly
            180                 185                 190

Gly Thr Tyr Glu Asn Arg Asp Val Ile Asn Arg Phe Asn Leu Ala Val
        195                 200                 205

Val Asn Thr Ile Arg Ala Ser Gly Gly Asn Asn Asp Lys Arg Phe Ile
    210                 215                 220

Leu Val Pro Thr Asn Ala Ala Thr Gly Leu Asp Val Ala Leu Asn Asp
225                 230                 235                 240

Leu Val Ile Pro Asn Asn Asp Ser Arg Val Ile Val Ser Ile His Ala
                245                 250                 255

Tyr Ser Pro Tyr Phe Phe Ala Met Asp Val Asn Gly Thr Ser Tyr Trp
            260                 265                 270

Gly Ser Asp Tyr Asp Lys Ala Ser Phe Thr Ser Glu Leu Asp Ala Ile
        275                 280                 285

Tyr Asn Arg Phe Val Lys Asn Gly Arg Ala Val Ile Ile Gly Gly Phe
    290                 295                 300

Gly Thr Ile Asp Lys Asn Asn Leu Ser Ser Arg Val Ala His Ala Glu
305                 310                 315                 320

His Tyr Ala Arg Glu Ala Val Ser Arg Gly Ile Ala Val Phe Trp Trp
                325                 330                 335

Asp Asn Gly Tyr Tyr Asn Pro Gly Asp Ala Glu Thr Tyr Ala Leu Leu
            340                 345                 350

Asn Arg Arg Asn Leu Thr Trp Tyr Tyr Pro Glu Ile Val Gln Ala Leu
        355                 360                 365

Met Arg Gly Ala Gly Val Glu Gly Leu Asn Ala Thr Pro Thr Lys Gly
    370                 375                 380

Ala Thr Pro Thr Asn Thr Ala Thr Pro Thr Lys Ser Ala Thr Ala Thr
385                 390                 395                 400

Pro Thr Arg Pro Ser Val Pro Thr Val Ser Gly Asn Leu Lys Val Glu
                405                 410                 415
```

```
Phe Tyr Asn Ser Asn Pro Ser Asp Thr Thr Asn Ser Ile Asn Pro Gln
            420                 425                 430

Phe Lys Val Thr Asn Thr Gly Ser Ser Ala Ile Asp Leu Ser Lys Leu
        435                 440                 445

Thr Leu Arg Tyr Tyr Tyr Thr Val Asp Gly Gln Lys Asp Gln Thr Phe
    450                 455                 460

Trp Cys Asp His Ala Ala Ile Ile Gly Ser Asn Gly Ser Tyr Asn Gly
465                 470                 475                 480

Ile Thr Ser Asn Val Lys Gly Thr Phe Val Lys Met Ser Ser Ser Thr
                485                 490                 495

Asn Asn Ala Asp Thr Tyr Leu Glu Ile Ser Phe Thr Gly Gly Thr Leu
            500                 505                 510

Glu Pro Gly Ala His Val Gln Ile Gln Gly Arg Phe Ala Lys Asn Asp
        515                 520                 525

Trp Ser Asn Tyr Thr Gln Ser Asn Asp Tyr Ser Phe Lys Ser Ala Ser
    530                 535                 540

Gln Phe Val Glu Trp Asp Gln Val Thr Ala Tyr Leu Asn Gly Val Leu
545                 550                 555                 560

Val Trp Gly Lys Glu Pro Gly
                565
```

<210> SEQ ID NO 29
<211> LENGTH: 558
<212> TYPE: PRT
<213> ORGANISM: Artificial Sequence
<220> FEATURE:
<223> OTHER INFORMATION: Chemically synthesized; GH5_g5_ E310S_CBM3a

<400> SEQUENCE: 29

```
Met Gly Met Gly Ala Thr Asn Leu Thr Ala Ala Gln Ile Gln Arg Gly
1               5                   10                  15

Met Gly Leu Gly Phe Asn Ile Gly Asn Thr Phe Asp Ser Ser Asn Asn
            20                  25                  30

Asp Met Gly Cys Leu Val Ser Asn His Glu Leu His Trp Gly Asn Pro
        35                  40                  45

Ala Val Thr Gln Ala Tyr Val Asp Ala Ile Tyr Asp Lys Gly Phe Arg
    50                  55                  60

Ser Ile Arg Leu Pro Ile Thr Trp Tyr Glu Phe Ile Thr Glu Asp Asn
65                  70                  75                  80

Gly Thr Tyr Ser Ile Lys Pro Glu Tyr Leu Ala Arg Val Lys Glu Val
                85                  90                  95

Val Asp Tyr Ala Tyr Asn Lys Asn Met Tyr Val Ile Ile Asn Val His
            100                 105                 110

His Glu Asn Trp Ile Asn Arg Ser Asp Leu Ala Ala Ser Tyr Asn Ser
        115                 120                 125

Ile Ser Pro Lys Leu Lys Gly Val Trp Lys Val Ile Ala Glu Tyr Phe
    130                 135                 140

Ser Asp Tyr Asp Gln Arg Leu Ile Phe Glu Gly Met Asn Glu Pro Arg
145                 150                 155                 160

Leu Val Gly Val Glu Gly Val Glu Trp Val Gly Asn Ala Glu Ala Tyr
                165                 170                 175

Asn Val Val Asn Lys Leu Asp Lys Asp Phe Ile Ser Thr Val Arg Ser
            180                 185                 190

Val Ala Ser Pro Tyr Lys Ser Thr Arg Leu Leu Met Val Pro Ser Tyr
        195                 200                 205
```

```
Ala Ala Ser Val Asn Pro Val Ala Tyr Glu Lys Met Asp Met Thr Met
    210                 215                 220

Phe Asn Asp Pro Tyr Val Ala Ala Ser Ile His Ala Tyr Ser Pro Tyr
225                 230                 235                 240

Asn Phe Ala Met Gly Asn Gly Asp His Ser Asp Phe Ser Pro Tyr Lys
                245                 250                 255

Ala Glu Leu Glu Ser Ile Phe Ala Gly Leu Arg Thr Thr Phe Thr Ser
            260                 265                 270

Lys Lys Ile Pro Val Ile Leu Gly Ser Phe Ser Ser Ser Asn Phe Asn
        275                 280                 285

Asn Gln Ser Ala Arg Val Ala Trp Ala Lys Cys Tyr Met Glu Gln Ala
    290                 295                 300

Lys Lys Leu Gly Ile Pro Cys Val Leu Trp Asp Asn Asp Val Ile Ala
305                 310                 315                 320

Met Gln Asp Asp Gly Glu Ala His Gly Tyr Leu Asn Arg Ala Thr Asn
                325                 330                 335

Lys Trp Tyr Ser Glu Ser Glu Pro Val Val Asn Ala Leu Leu Ser Thr
            340                 345                 350

Leu Asn Asp Val Leu Asn Ala Thr Pro Thr Lys Gly Ala Thr Pro Thr
        355                 360                 365

Asn Thr Ala Thr Pro Thr Lys Ser Ala Thr Ala Thr Pro Thr Arg Pro
    370                 375                 380

Ser Val Pro Thr Asn Thr Pro Thr Asn Thr Pro Ala Asn Thr Pro Val
385                 390                 395                 400

Ser Gly Asn Leu Lys Val Glu Phe Tyr Asn Ser Asn Pro Ser Asp Thr
                405                 410                 415

Thr Asn Ser Ile Asn Pro Gln Phe Lys Val Thr Asn Thr Gly Ser Ser
            420                 425                 430

Ala Ile Asp Leu Ser Lys Leu Thr Leu Arg Tyr Tyr Tyr Thr Val Asp
        435                 440                 445

Gly Gln Lys Asp Gln Thr Phe Trp Cys Asp His Ala Ala Ile Ile Gly
    450                 455                 460

Ser Asn Gly Ser Tyr Asn Gly Ile Thr Ser Asn Val Lys Gly Thr Phe
465                 470                 475                 480

Val Lys Met Ser Ser Ser Thr Asn Asn Ala Asp Thr Tyr Leu Glu Ile
                485                 490                 495

Ser Phe Thr Gly Gly Thr Leu Glu Pro Gly Ala His Val Gln Ile Gln
            500                 505                 510

Gly Arg Phe Ala Lys Asn Asp Trp Ser Asn Tyr Thr Gln Ser Asn Asp
        515                 520                 525

Tyr Ser Phe Lys Ser Ala Ser Gln Phe Val Glu Trp Asp Gln Val Thr
    530                 535                 540

Ala Tyr Leu Asn Gly Val Leu Val Trp Gly Lys Glu Pro Gly
545                 550                 555
```

<210> SEQ ID NO 30
<211> LENGTH: 572
<212> TYPE: PRT
<213> ORGANISM: Artificial Sequence
<220> FEATURE:
<223> OTHER INFORMATION: Chemically synthesized; GH5_g10_E313G_CBM3a -continued

<400> SEQUENCE: 30

```
Met Pro Ala Lys Thr Val Tyr Ala Ala Gly Thr Asp Lys Thr Ala Thr
1               5                   10                  15

Glu Val Val Ser Asp Met Thr Val Gly Trp Asn Leu Gly Asn Ser Leu
            20                  25                  30

Asp Ser Tyr Gly Gln Ser Ser Asn Phe Pro Tyr Thr Ser Ser Asn Glu
        35                  40                  45

Thr Tyr Trp Gly Asn Pro Lys Thr Thr Lys Ala Leu Ile Asp Ala Val
    50                  55                  60

Ala Glu Ala Gly Phe Asn Thr Ile Arg Ile Pro Val Ser Trp Gly Gln
65                  70                  75                  80

Tyr Thr Thr Gly Ser Asp Tyr Gln Ile Pro Asp Phe Phe Met Ser Arg
                85                  90                  95

Val Lys Glu Val Val Asp Tyr Ala Ile Ala Asn Asp Met Tyr Val Ile
            100                 105                 110

Leu Asn Thr His His Asp Ile Asn Ser Asp Tyr Cys Phe Tyr Val Pro
        115                 120                 125

Asn Asn Ala Asn Lys Asp Arg Ser Glu Lys Tyr Phe Asn Ser Ile Trp
    130                 135                 140

Thr Gln Val Ala Asn Glu Phe Lys Asn Tyr Asp Tyr His Leu Val Phe
145                 150                 155                 160

Glu Thr Met Asn Glu Pro Arg Leu Val Gly His Ser Glu Glu Trp Trp
                165                 170                 175

Phe Pro Arg Asn Asn Pro Ser Ser Asp Ile Lys Glu Ala Val Ala Cys
            180                 185                 190

Ile Asn Asp Tyr Asn Gln Val Ala Leu Asp Ala Ile Arg Ala Thr Gly
        195                 200                 205

Gly Asn Asn Ala Thr Arg Cys Val Met Val Pro Gly Tyr Asp Ala Ser
    210                 215                 220

Ile Glu Gly Cys Met Thr Asp Gly Phe Lys Met Pro Lys Asp Ser Ala
225                 230                 235                 240

Ser Asn Arg Leu Ile Leu Ser Val His Ala Tyr Ile Pro Tyr Thr Phe
                245                 250                 255

Ala Leu Ala Ser Asp Thr Tyr Thr Lys Thr Phe Ser Asp Asn Leu Lys
            260                 265                 270

Gly Asp Ile Asp Ser Phe Phe Asn Asp Leu Asp Ser Lys Phe Leu Ser
        275                 280                 285

Lys Asn Ile Pro Val Val Val Gly Gly Thr Ser Ala Thr Asn Arg Asn
    290                 295                 300

Asn Lys Asp Glu Arg Val Lys Trp Ala Asp Tyr Tyr Trp Gly Ala Ala
305                 310                 315                 320

Ala Lys His Ser Asn Val Ala Met Val Leu Trp Asp Asn Asn Val Tyr
                325                 330                 335

Glu Asn Asn Ser Ala Gly Ser Asn Gly Glu Cys His Met Tyr Ile Asp
            340                 345                 350

Arg Asn Ser Leu Gln Trp Lys Asp Pro Glu Ile Ile Ser Ala Ile Met
        355                 360                 365

Lys Val Leu Asn Ala Thr Pro Thr Lys Gly Ala Thr Pro Thr Asn Thr
    370                 375                 380

Ala Thr Pro Thr Lys Ser Ala Thr Ala Thr Pro Thr Arg Pro Ser Val
385                 390                 395                 400

Pro Thr Asn Thr Pro Thr Asn Thr Pro Ala Asn Thr Pro Val Ser Gly
                405                 410                 415
```

-continued

```
Asn Leu Lys Val Glu Phe Tyr Asn Ser Asn Pro Ser Asp Thr Thr Asn
            420                 425                 430

Ser Ile Asn Pro Gln Phe Lys Val Thr Asn Thr Gly Ser Ser Ala Ile
        435                 440                 445

Asp Leu Ser Lys Leu Thr Leu Arg Tyr Tyr Tyr Thr Val Asp Gly Gln
    450                 455                 460

Lys Asp Gln Thr Phe Trp Cys Asp His Ala Ala Ile Ile Gly Ser Asn
465                 470                 475                 480

Gly Ser Tyr Asn Gly Ile Thr Ser Asn Val Lys Gly Thr Phe Val Lys
                485                 490                 495

Met Ser Ser Ser Thr Asn Asn Ala Asp Thr Tyr Leu Glu Ile Ser Phe
            500                 505                 510

Thr Gly Gly Thr Leu Glu Pro Gly Ala His Val Gln Ile Gln Gly Arg
        515                 520                 525

Phe Ala Lys Asn Asp Trp Ser Asn Tyr Thr Gln Ser Asn Asp Tyr Ser
    530                 535                 540

Phe Lys Ser Ala Ser Gln Phe Val Glu Trp Asp Gln Val Thr Ala Tyr
545                 550                 555                 560

Leu Asn Gly Val Leu Val Trp Gly Lys Glu Pro Gly
                565                 570
```

ENGINEERED CARBOHYDRATE-ACTIVE ENZYMES FOR GLYCAN POLYMERS SYNTHESIS

CROSS-REFERENCE TO RELATED APPLICATIONS

This application claims priority under 35 U.S.C. § 119(e) to U.S. Provisional Patent Application No. 62/719,963, filed Aug. 20, 2018, the contents of which are incorporated by reference herein in their entirety.

STATEMENT REGARDING FEDERALLY SPONSORED RESEARCH OR DEVELOPMENT

This invention was made with Government support under Grant Number 1704679 awarded by the National Science Foundation. The Government has certain rights in this invention.

SEQUENCE LISTING The ASCII text file named "370602-7008US1-Sequence-Listing-text.txt" created on Aug. 19, 2019, comprising 107 kilobytes, is hereby incorporated by reference in its entirety.

BACKGROUND OF THE INVENTION

Synthesis of glycan-based polymers (oligosaccharides and polysaccharides) using engineered carbohydrate-active enzymes (CAZymes) offers exquisite regioselective and stereoselective control over traditional synthetic chemistry approaches, which are atom inefficient and involve multi-step transformations. Glycosyltransferases (GTs) are naturally occurring CAZymes that synthesize glycans but give poor heterologous expression yields, have narrow substrate specificity, and use expensive nucleotide sugars, that limiting the scale-up of in vitro glycans synthesis.

Chemoenzymatic synthesis using glycosyl hydrolases (GH) could permit production of complex glycans at high yields. GH are nature's antipodes of GT by hydrolyzing glycosidic linkages, but can also produce glycans via transglycosylation if the nucleophilic water is replaced by a sugar molecule as an acceptor. Unfortunately, transglycosylation suffers from low yields since the product is also a substrate for GH-mediated hydrolysis. However, most GH have plasticity in their structure, which allows for improving synthase activity.

Interestingly, glycosynthases (GSs) offer an alternative biosynthetic approach to producing glycans in a facile manner. The GSs are mutants of readily available microbial glycosyl hydrolases (GHs), which are incapable of hydrolyzing glycosidic bonds, and can be engineered to specifically synthesize complex glycans. However, to date, only a limited number of GSs have been created from wild-type GHs using an inefficient empirical strategy that have limited biosynthetic activity.

Unlike GTs, there is a much larger selection of GHs available that can be expressed readily in *E. coli*. Further, the active site GH nucleophile residue can be mutated to prevent product hydrolysis and improve product yields. However, the role of various accessory domains on the transglycosylation activity of mutant GH/GS is mostly unknown.

Thus, there is a need in the art for constructs engineered to enhance the efficiency of glycan polymer synthesis. The present invention fulfills this need.

BRIEF SUMMARY OF THE INVENTION

The invention provides a construct comprising a Glycoside Hydrolase (GH) catalytic domain (CD). In certain embodiments, the CD is conjugated to a carbohydrate binding module 3a (CBM3a). In other embodiments, the CD is mutated with respect to its wild-type form so that the mutated CD is capable of catalyzing glycan polymer synthesis.

The invention further provides a method for promoting glycan polymer synthesis. In certain embodiments, the method comprises contacting a glycosyl donor substrate with an effective amount of any construct contemplated in the invention.

BRIEF DESCRIPTION OF THE DRAWINGS

The following detailed description of illustrative embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 2C illustrates a comparison of reaction kinetics for glycan polymer synthesis catalyzed by CelE-E316G and CelE-E316G tagged with CBM1, CBM17, or CBM3a.

FIG. 2D illustrates rate constants for glycan polymer synthesis catalyzed by CelE E316G and CelE E316G tagged with CBM1, CBM17, or CBM3a.

FIG. 8 illustrates a plasmid map for pEC_CelE_CBM3a.

DETAILED DESCRIPTION OF THE INVENTION

Figure 1A:
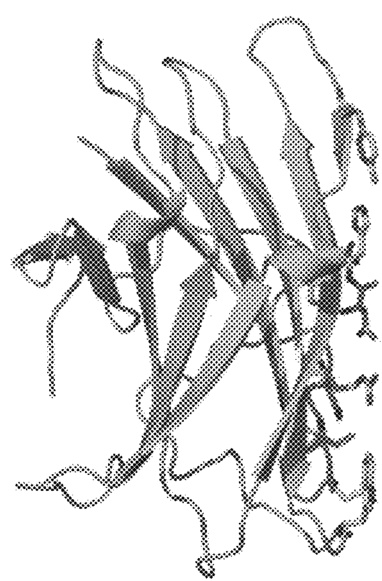
FIG. 1A illustrates a ribbon diagram representing structure of carbohydrate binding module 3a (CBM3a).
Figure 1B:
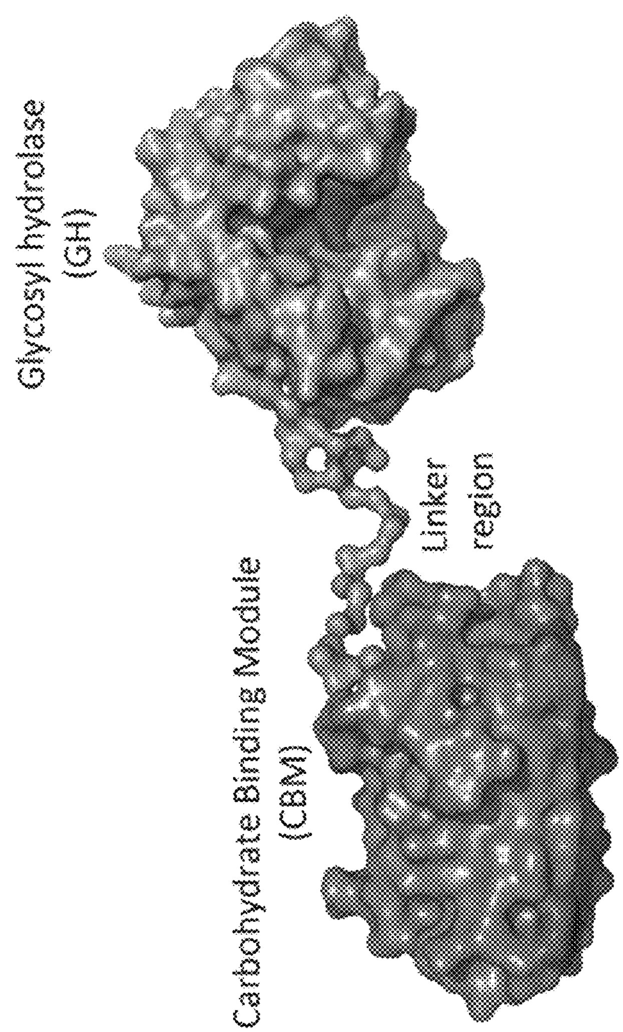
FIG. 1B illustrates a space-filling model representation of a carbohydrate binding module (CBM) and GH connected via a linker.

The present invention relates, in one aspect, to the discovery of certain constructs that function as Carbohydrate-Active Enzyme constructs (CAZymes). In certain embodiments, the constructs of the invention comprise a catalytic domain (CD) conjugated to a carbohydrate binding module (CBM) of a glycosyl hydrolase (GH). In other embodiments, the CD is mutated so as to have reduced, insignificant, or no glycan hydrolytic activity. In yet other embodiments, the constructs of the invention have enhanced transglycosylation activity as compared to the CD.

In certain other embodiments, the invention provides a method for promoting glycan polymer synthesis using the constructs of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, illustrative methods and materials are described. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The following notation conventions are applied to the present disclosure for the sake of clarity. In any case, any teaching herein that does not follow this convention is still part of the present disclosure, and can be fully understood in view of the context in which the teaching is disclosed. Protein symbols are disclosed in non-italicized capital letters. As non-limiting example, "CelE" refer to the protein. Notations about mutations are shown as uppercase text. As non-limiting example, "E316G" refer to mutated site 316, where in a glutamic acid residue is replaced with a glycine residue.

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

As used herein the terms "alteration," "defect," "variation," or "mutation" refer to a mutation in a gene in a cell that affects the function, activity, expression (transcription or translation) or conformation of the polypeptide it encodes, including missense and nonsense mutations, insertions, deletions, frameshifts and premature terminations.

As used herein, the terms "conservative variation" or "conservative substitution" as used herein refers to the replacement of an amino acid residue by another biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, the terms "effective amount," refer to a nontoxic but sufficient amount of an agent to provide the desired results. That result may be enhancing the rate of reaction, increasing purity of the product, increasing the yield of the product As used herein, the term "fragment," as applied to a nucleic acid, refers to a subsequence of a larger nucleic acid. A "fragment" of a nucleic acid can be at least about 15, 50-100, 100-500, 500-1000, 1000-1500 nucleotides, 1500-2500, or 2500 nucleotides (and any integer value in between). As used herein, the term "fragment," as applied to a protein or peptide, refers to a subsequence of a larger protein or peptide, and can be at least about 20, 50, 100, 200, 300 or 400 amino acids in length (and any integer value in between).

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Instructional material," as that term is used herein, includes a publication, a recording, a diagram, or any other medium of expression that can be used to communicate the usefulness of the nucleic acid, peptide, and/or compound of the invention in the kit for identifying or alleviating or treating the various diseases or disorders recited herein.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide.

As used herein, the term "polypeptide" refers to a polymer composed of amino acid residues, related naturally occurring structural variants, and synthetic non-naturally occurring analogs thereof linked via peptide bonds.

As used herein, "substantially purified" refers to being essentially free of other components. For example, a substantially purified polypeptide is a polypeptide that has been separated from other components with which it is normally associated in its naturally occurring state. Non-limiting embodiments include 95% purity, 99% purity, 99.5% purity, 99.9% purity and 100% purity.

As used herein, the term "wild-type" refers to a gene or gene product isolated from a naturally occurring source. A wild-type gene is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Constructs

In one aspect, the invention provides a construct comprising a CD (from a GH) conjugated to a carbohydrate binding module (CBM, such as but not limited to CBM3a). In certain embodiments, the CD is conjugated to the CBM via a linker, such that the construct having the CBM shows enhanced transglycosylation activity compared to the corresponding constructs that are either devoid of a CBM, or include a CBM other than the CBM3a.

In certain embodiments, the CD is from a GH family member that shows activity either on cello-oligosaccharides or cellulose. The GH families active either on cello-oligosaccharides or cellulose include, but are not limited to, GH5, GH7, GH8, and GH12.

In certain embodiments, *Clostridium thermocellum* Cthe_0797, also called CelE, a member of GH5 family, is used within the constructs of the invention. The CD from native CelE is capable of hydrolyzing cellulose, mannan, galactomannan, and/or xylan substrates.

Figure 2A:
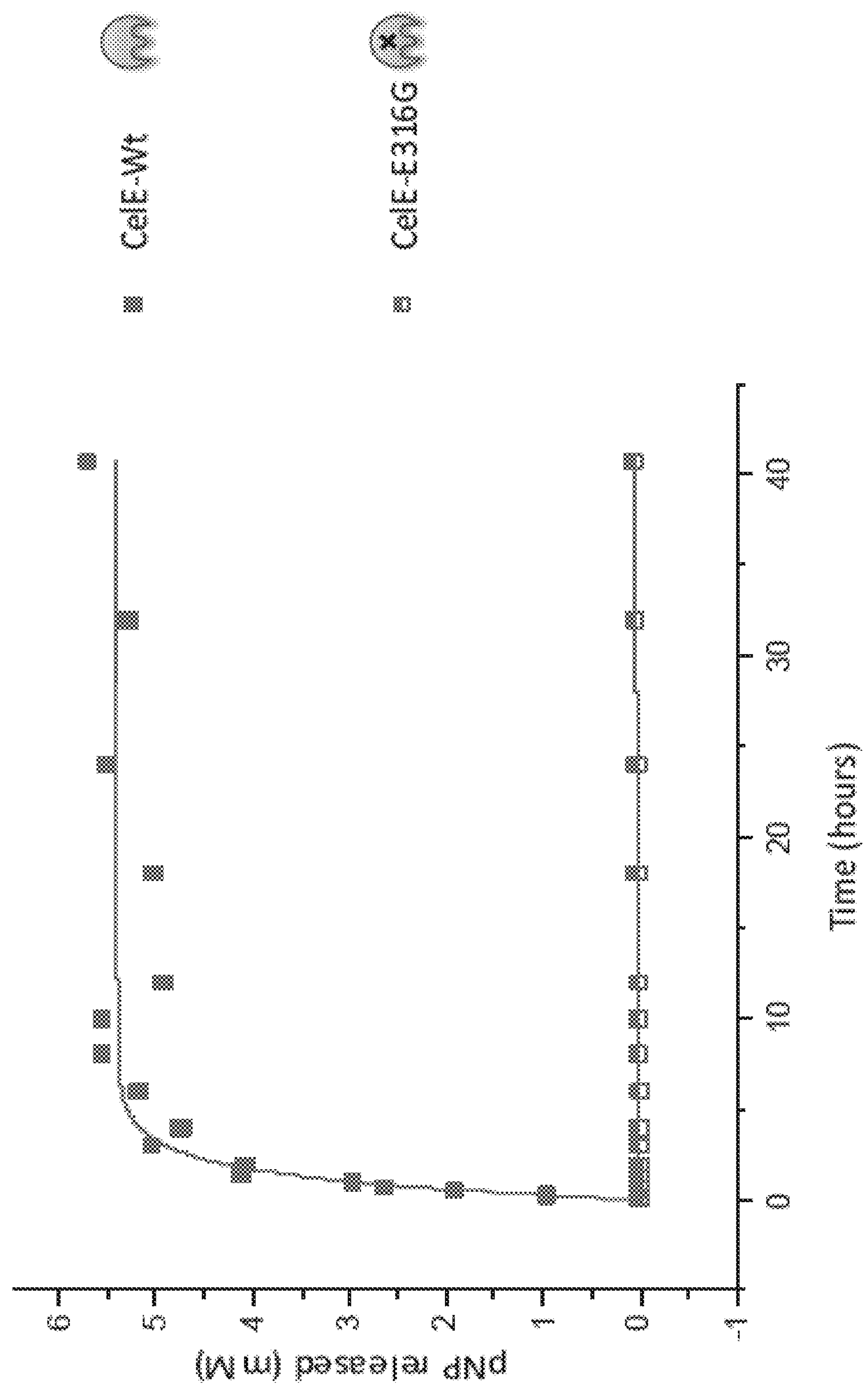
FIG. 2A shows that mutating a nucleophilic residue of CelE-wt to a non-nucleophilic residue (E316G) eliminates 95% of hydrolase activity.

In certain embodiments, the CD comprises at least one mutation, such that a catalytic nucleophilic amino acid residue is mutated to a non-nucleophilic amino acid residue, so as to suppress the hydrolysis activity of the CD while enhancing the transglycosylation activity thereof. For example, CelE-E316G suppresses the hydrolysis activity of wt CelE, as shown in FIG. 2A. In other embodiments, the catalytic acid/base residue of the CD is mutated. For example, a point mutation, E193A, is introduced in the CD from GH5 to improve the transglycosylation activity thereof.

In certain embodiments, the CD is conjugated to the CBM3a through a peptidic linker. In other embodiments, the CD is conjugated to other CBMs, such as but not limited to, CBM1 or CBM 17, through a peptidic linker. In yet other embodiments, the length and the composition of the linker is chosen such that the CD and the CBM3a can function in coordinated fashion to enhance the transglycosylation activity of the CD. In yet other embodiments, the length of the linker ranges from about 7-200 amino acids. In yet other embodiments, the length of the linker ranges from about 15-41 amino acids. In yet other embodiments, the length of the linker is about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, an/or about 200 amino acids.

In certain embodiments, the N-terminus of the CD is conjugated to the C-terminus of the CBM through the linker. In other embodiments, the C-terminus of the CD is conjugated to the N-terminus of the CBM through the linker.

Figure 2B:
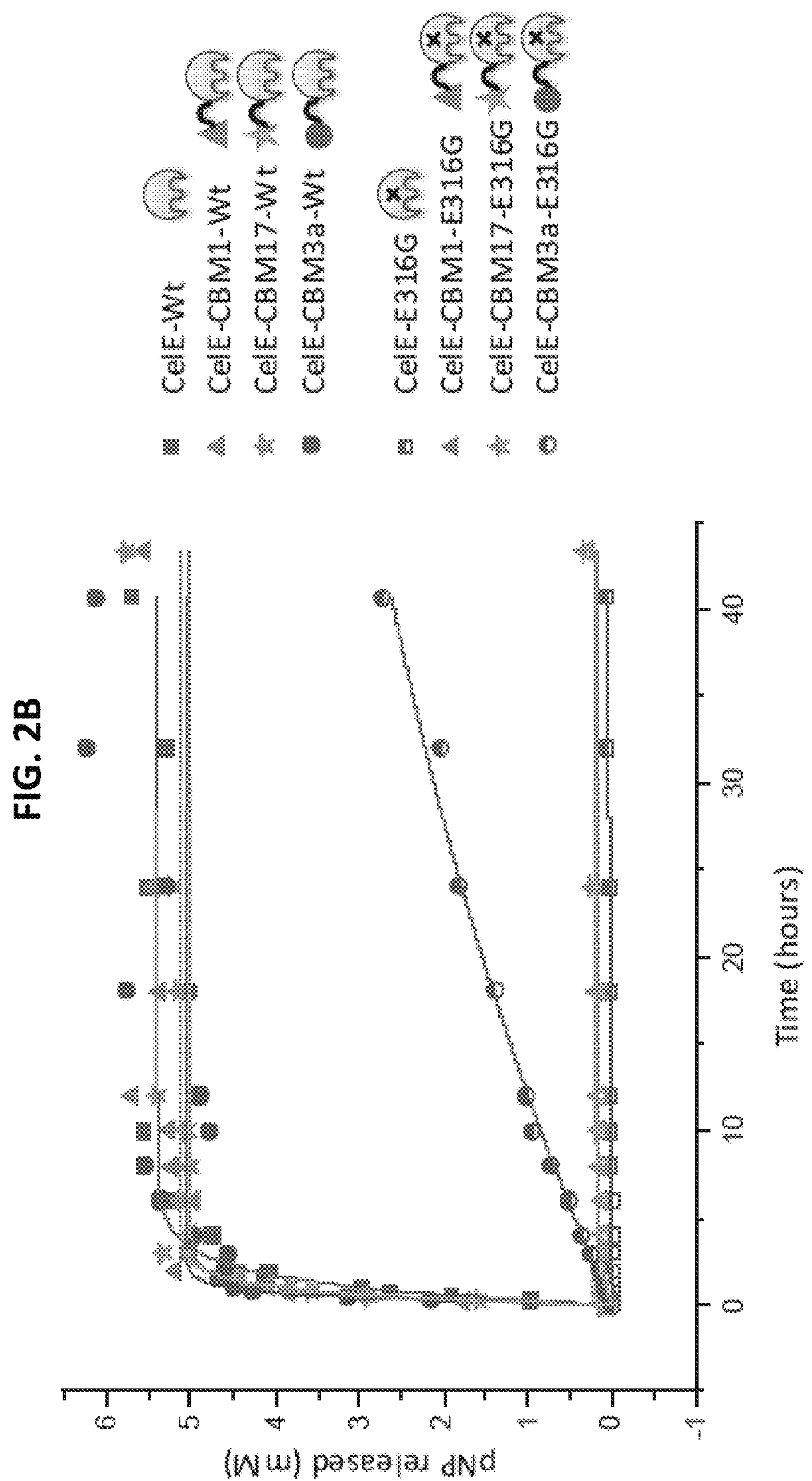
FIG. 2B shows that different CBMs (CBM1, CBM17, and CBM3a) have distinct effect on kinetics of glycan polymer synthesis.
Figures 2C, 2D:
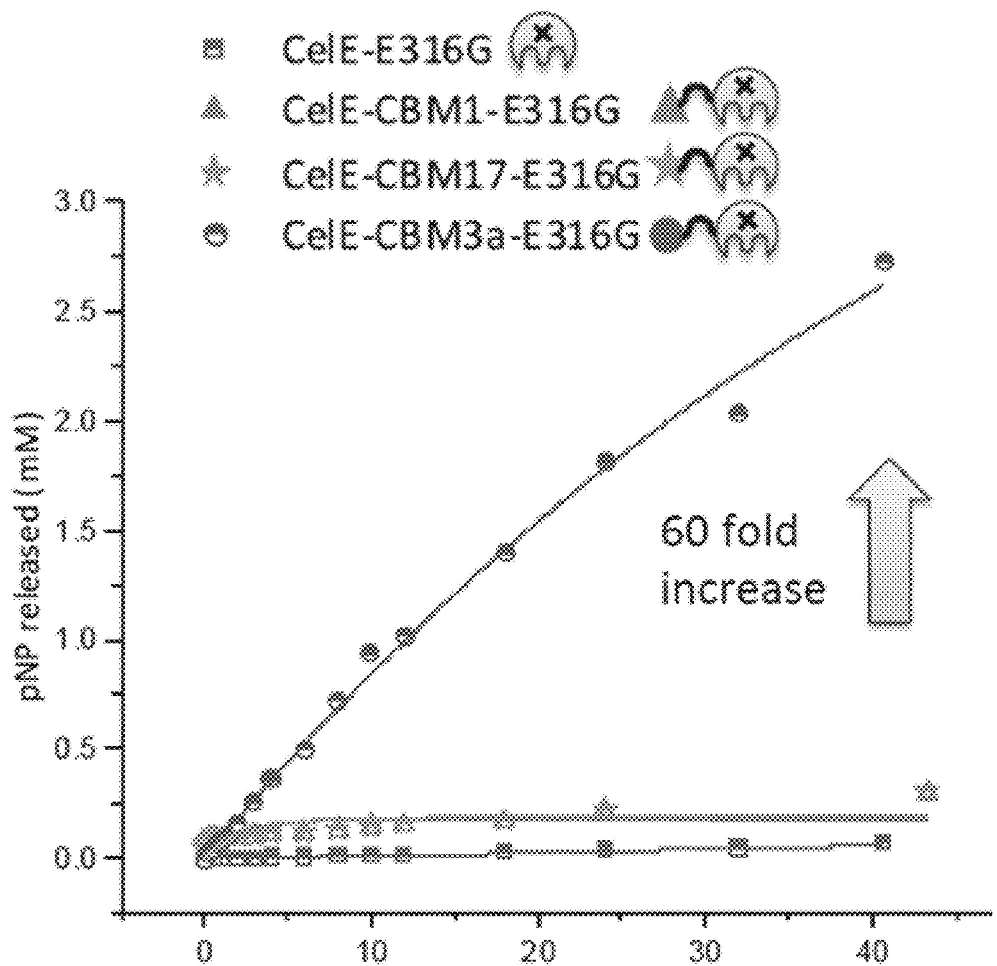

In certain embodiments, the constructs having CD conjugated to CBM show at least 2-fold higher glycan polymer synthesis activity than the corresponding wt constructs (such as, for example, CD not conjugated to the CBM). In other embodiments, the construct comprising CBM3a showed ~60 fold higher glycan polymer synthesis activity compared to either the wt construct or the mutant construct tagged with other CBMs, such as CBM 1 or CBM 17 as shown in FIGS. 2*b* and 2*c*.

In one aspect, the construct of the invention comprises the CD from GH5, which comprises the point mutation E316G and is conjugated to CBM3a through a 41 amino acid long linker.

In certain embodiments, the construct comprises a CBM3a-linker polypeptide encoded by the nucleotide sequence of any of SEQ ID NOs. 1, 3, 5, 7, 9, 11, 13.

In certain embodiments, the construct comprises a CBM3a-linker polypeptide with at least about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% homology with the amino acid sequence of any of SEQ ID NOs. 2, 4, 6, 8, 10, 12, 14.

In certain embodiments, the construct comprises a CBM3a-linker polypeptide with at least about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% identity with the amino acid sequence of any of SEQ ID NOs. 2, 4, 6, 8, 10, 12, 14.

In certain embodiments, the construct comprises a polypeptide that is encoded by the nucleotide sequence of any of SEQ ID NOs. 1, 3, 5, 7, 9, 11, 13, 15, 17, 19, 21, 23, 25, 27.

In certain embodiments, the construct comprises a polypeptide with at least about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% homology with the amino acid sequence of any of SEQ ID NOs. 2, 4, 6, 8, 10, 12, 14, 16, 18, 20, 22, 24, 26, 28, 29, 30.

In certain embodiments, the construct comprises a polypeptide with at least about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% identity with the amino acid sequence of any of SEQ ID NOs. 2, 4, 6, 8, 10, 12, 14, 16, 18, 20, 22, 24, 26, 28, 29, 30.

Methods

In one aspect, the invention provides a method for catalyzing glycan polymer synthesis. In certain embodiments, the method comprises contacting a glycosyl donor substrate with an effective amount of a construct of the invention. In other embodiments, the substrate includes includes for example, cellobiose, glucose, xylose, and mannose.

In certain embodiments, the CD is from a GH family member that can produce sugars such as cello-oligosaccharides and/or cellulose. The GH families that can produce sugars such as cello-oligosaccharides and/or cellulose include for example GH5, GH7, GH8, and/or GH12.

In certain embodiments, *Clostridium thermocellum* Cthe_0797, also called CelE, a member of GH5 family, is used within the constructs of the invention. The CD from native CelE is capable of hydrolyzing cellulose, mannan, galactomannan, and/or xylan substrates.

In certain embodiments, the CD comprises at least one mutation wherein a catalytic nucleophilic amino acid residue is mutated to a non-nucleophilic amino acid residue so as to suppress the hydrolysis activity of the CD while enhancing its transglycosylation activity. For example, CelE-E316G suppresses the hydrolysis activity of wt CelE, as shown in FIG. 2A. In other embodiments, a catalytic acid/base residue of the CD is mutated. For example, a point mutation, E193A, is introduced in the CD from GH5 to improve its transglycosylation activity.

In certain embodiments, the CD is conjugated to the CBM3a through a peptidic linker. In other embodiments, the CD is conjugated to other CBMs, such as but not limited to, CBM1 or CBM 17, through a peptidic linker. In yet other embodiments, the length and the composition of the linker is chosen such that the CD and the CBM3a can function in coordinated fashion to enhance the transglycosylation activity of the CD. In yet other embodiments, the length of the linker ranges from about 7-200 amino acids. In yet other embodiments, the length of the linker ranges from about 15-41 amino acids.

In certain embodiments, the N-terminus of the CD is conjugated to the C-terminus of the CBM through the linker. In other embodiments, the C-terminus of the CD is conjugated to the N-terminus of the CBM through the linker.

In certain embodiments, the constructs having CD conjugated to CBM show at least 2-fold higher glycan polymer synthesis activity than the corresponding wt constructs (such as, for example, CD not conjugated to the CBM). In other embodiments, the construct comprising CBM3a showed ~60 fold higher glycan polymer synthesis activity compared to either the wt construct or the mutant construct tagged with other CBMs, such as CBM 1 or CBM 17 as shown in FIGS. 2*b* and 2*c*.

In one aspect, the construct of the invention comprises the CD from GH5, which comprises the point mutation E316G and is conjugated to CBM3a through a 41 amino acid long linker.

In certain embodiments, the construct of the invention enhances the rate constant (k) of the glycan synthesis reaction. For example, as calculated in FIG. 2C, the k value (in mM/hr) for CelE-CBM3a-E316G construct, is 0.0834 ($\pm 8.40\times10^{-7}$), much higher than the CelE-E316G, CelE-CBM1-E316G and CelE-CBM17-E316G constructs, which show k values of 0.0014 ($\pm 6.64\times10^{-5}$),0.0054 ($\pm 1.84\times10^{-4}$) and 0.0053 ($\pm 1.44\times10^{-4}$), respectively.

In another aspect, the invention provides a method of making a construct of the invention. In certain embodiments, the method comprises (a) linking a CD from a GH5, which comprises the point mutation E316G, to a CBM3a though a peptidic linker.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and assaying conditions with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the preferred embodiments of the present invention, and are not to be construed as limiting in any way the remainder of the disclosure.

Materials and Methods

Generating DNA Constructs Via Site-Directed Mutagenesis

Purification of wt DNA from *E. coli*

Figure 8:
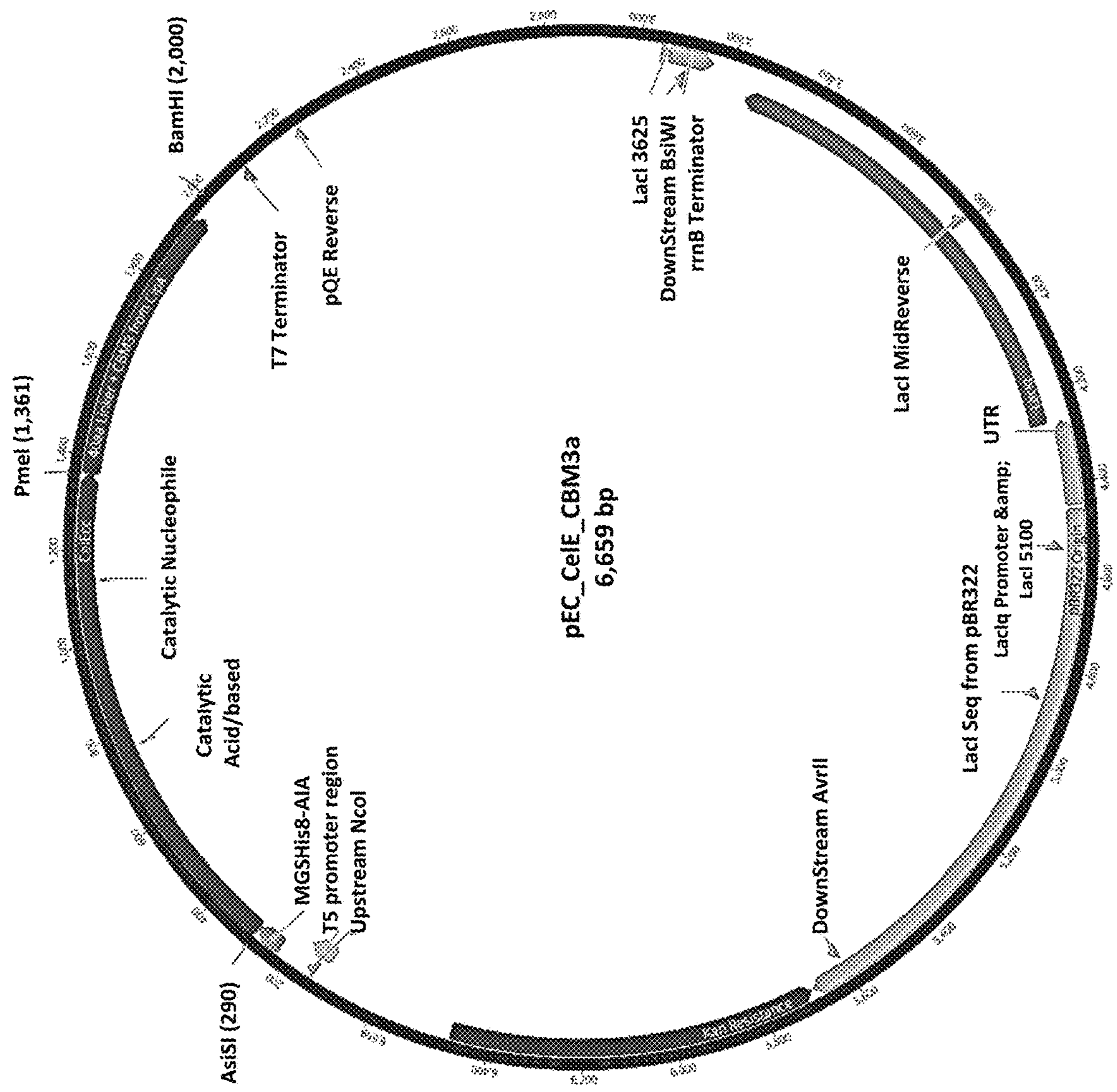
Figure 9:
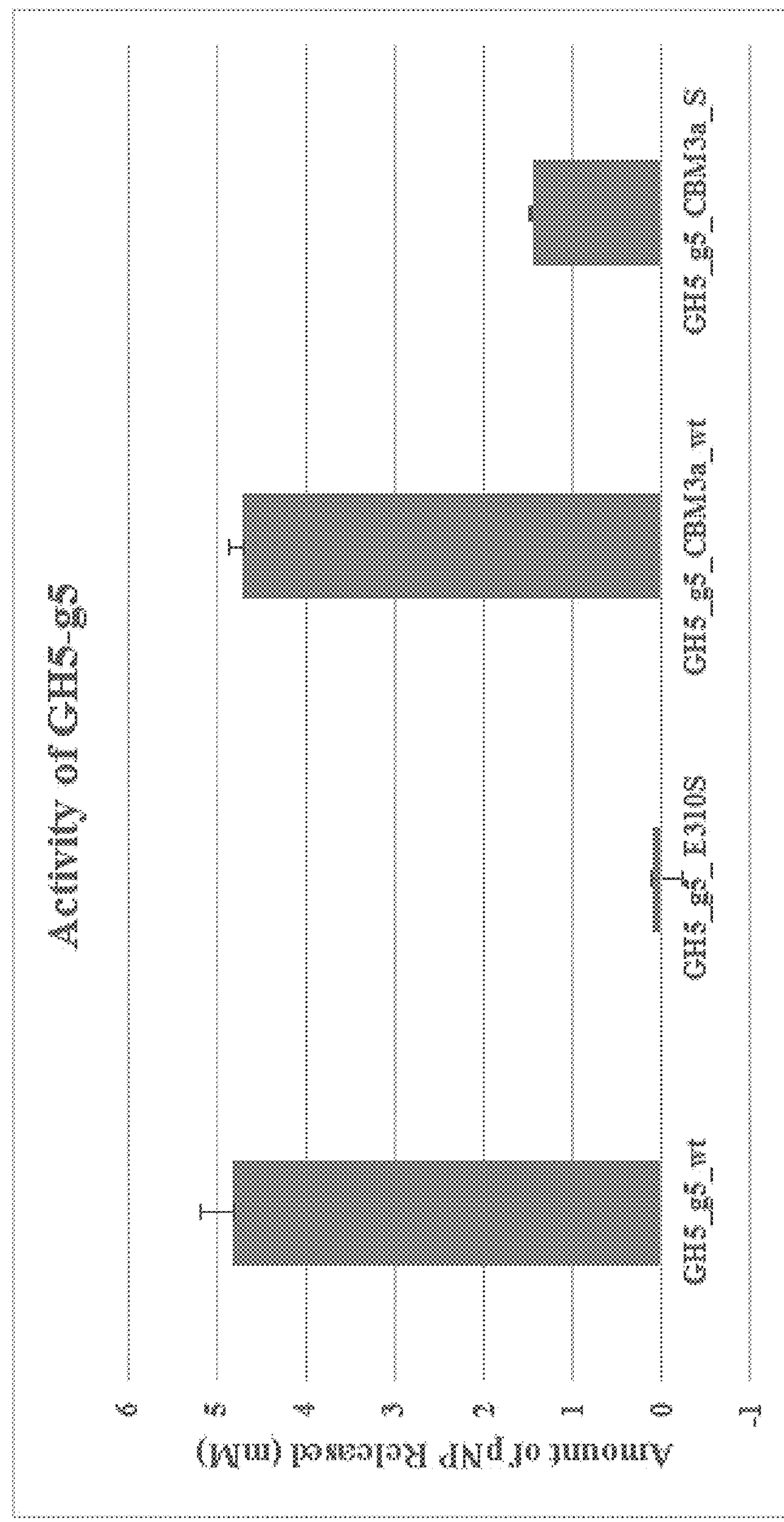
FIG. 9 illustrates activities based on product release for certain GH5-g5 constructs, which belong to same GH5 family as CelE and are phylogenetically related. The addition of CBM3a module to GH5-g5 improved the activity.
Figure 10:
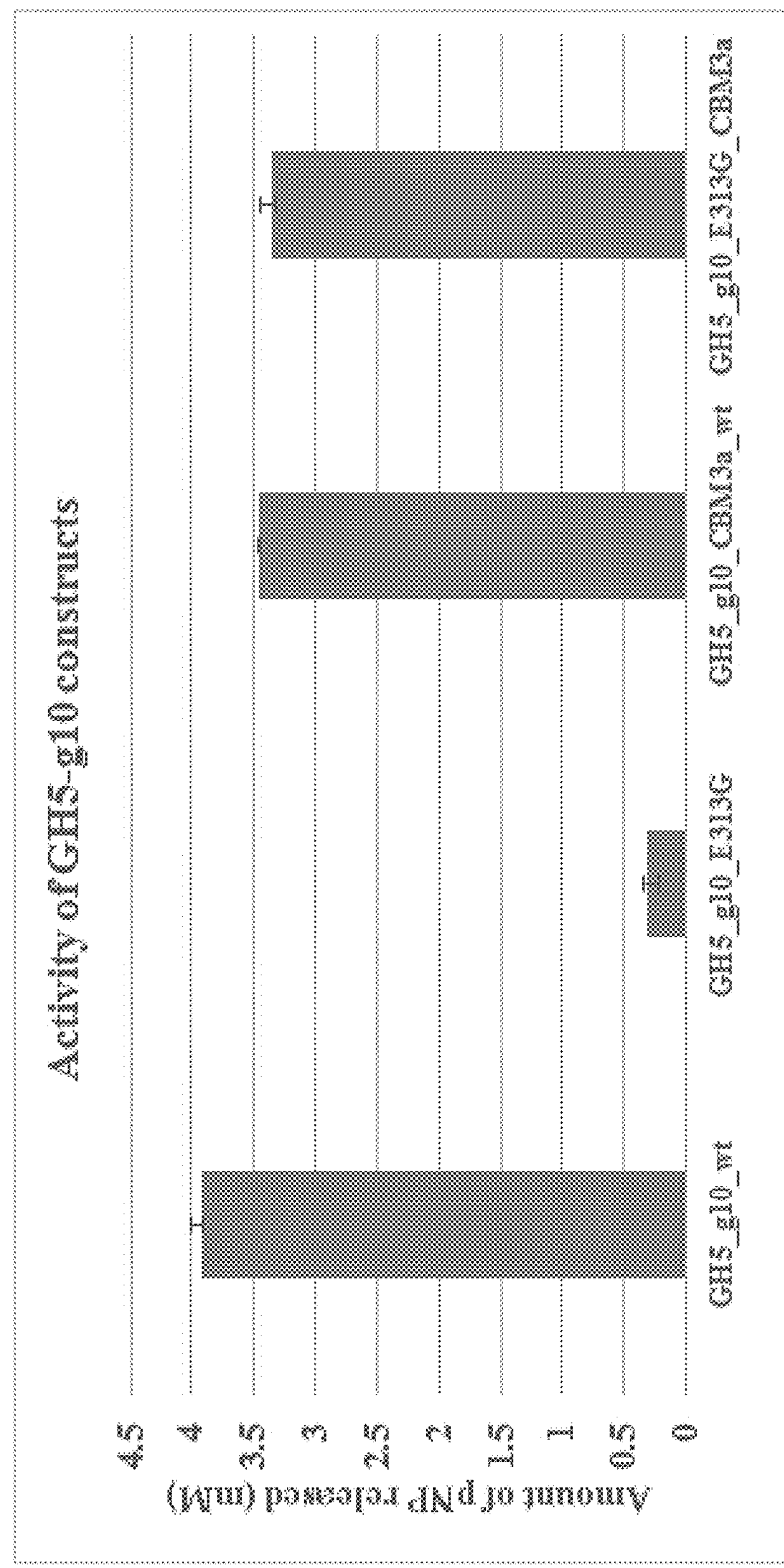
FIG. 10 illustrates activities based on product release for certain GH5-g10 constructs which belong to same GH5 family as CelE and are phylogenetically related. The addition of CBM3a module to GH5-g10 improved the activity.

The sequences encoding for CelE and CelE_CBM3a were incorporated in pEC plasmid backbone, as shown in FIG. 8. The plasmids were transformed into *E. coli* BL21, and the transformants were stored into glycerol stocks. To create the mutant DNA constructs, the wt plasmids were extracted from *E. Coli* BL21, purified, and subjected to the site-directed mutagenesis to mutate the nucleophilic amino acid. To extract the wt plasmid from *E. coli* and to remove the genomic DNA and RNA, a Geneaid miniprep kit was used.

Purification of wt plasmids involved the steps of (a) lysing the cells and removing the DNA, RNA filled supernatant, (b)

digesting the RNA with RNase A, and (c) precipitating the proteins. A centrifugation step was then used to remove precipitated proteins and genomic DNA from the plasmids. The supernatant which contained the plasmid was then fed into a silica gel plasmid spin column to wash the plasmids of salts and RNA. The plasmids were then extracted from the silica gel and are sent for sequencing to confirm that all wt DNA constructs are correct.

Site-Directed Mutagenesis

Once the wt DNA plasmids were purified, site-directed mutagenesis was performed, using PCR, to mutate the nucleophilic residues within the GH, forward and reverse primers having a one nucleotide mismatch that encodes for a change of nuclephilic amino acid to non-nucleophilic amino acid were used. At least 20 PCR cycles were performed with a denaturing step at 98° C. for 10 seconds, an annealing step of 66° C. for 30 seconds and an extension step at 72° C. for 210 seconds, new plasmids containing this mutation were created. To ensure the PCR was successful, DNA electrophoresis was used to check the size of the product.

Transformation & Testing for Positive Mutations

Competent *E. coli* cells were transformed with a plasmid using the heat shock transformation method. Two different types of competent cells were used, each type has been metabolically modified to serve different purposes. The *E. cloni* strain of *E. coli* was used initially since it is better for plasmid extraction and will be used to test for an effective nucleophilic mutation. *E. cloni* cells have been metabolically modified to remove pathways that can be used to digest foreign DNA. The BL21 strain of *E. coli* was used for protein expression. The *E. cloni* cells were plated onto a carboxymethyl cellulose (CMC) plate to test for a positive mutation. After growing on the plate, negative mutations with the nucleophilic residue were able to hydrolyze CMC, which created a circle on the plate once the plates were dyed with a Congo Red dye. Positive mutations were then grown to produce glycerol stocks of *E. cloni* cells, and for plasmid extraction for the transformation into BL21 cells.

Protein Expression

The gene encoding for each protein of interest is regulated by the lac operon repressor. Once cells growing in a 500 ml LB media culture have reached the secondary growth phase, the induction of protein expression on the lac operon was induced by the introduction of 0.5 mM of Isopropyl β-D-1-thiogalactopyranoside (IPTG). IPTG binds to the lac operon repressor, removing it from the lac operon promoter to allow for expression of the protein of interest in each individual culture.

Protein Extraction and Purification

Each protein was extracted from BL21 cells using a combination of mechanical and chemical extraction. The method of mechanical extraction as sonication, which is a method that uses ultrasonic vibration to burst cells in a liquid media. The method of chemical extraction uses lysozyme, which is an enzyme that catalyzes the destruction of bacterial cell walls. Both these methods were used to ensure the effective lysis of BL21 cells. Along with lysozyme, a protease inhibitor cocktail was added to the cells to ensure that the proteins of interest are not lysed by proteases once they leave the cells. The proteins were then centrifuged and filtered with a 0.22-micron filter to remove inclusion bodies and other large cell components.

The next step on protein production was to purify the proteins of interest from other proteins found in the cell. High-performance liquid chromatography (HPLC) was used to do the initial purification steps. HPLC for these proteins of interest was done with an immobilized metal affinity chromatography (IMAC) column. This chromatography method works for the proteins of interest because CelE is complexed to a chain of histidine residue on the C-terminus of the protein. The histidine residues form a complex with the nickel found in the IMAC column. Then to wash away foreign proteins, a solvent containing a low level of imidazole is passed through the column. Imidazole binds to the empty column sites and washes away proteins not bound to the column. Finally, to elute the proteins, a solvent containing a higher level of imidazole is passed through the column. Since imidazole and histidine has a very similar structure, the imidazole can displace the histidine from the nickel binding sites and elutes it from the column. Following immobilized metal affinity chromatography, gel filtration chromatography was done to decrease concentration of salts in the protein solution. Gel filtration chromatography works by allowing the flow of large macromolecules like proteins but, traps small molecules like salts in the gel pores. After gel filtration, the absorbance of each protein is measured using a spectrophotometer to calculate the concentration and then proteins are frozen for future use.

Sequences for certain wild-type and mutant constructs are listed below. In certain embodiments, stop codons located at the end of the nucleotide sequences (such as, but not limited to, TAG, TAA, TGA) can be removed from the sequences contemplated herein.

```
Wild type sequences (no mutation of catalytic
nucleophile residue, only CBM-linker variations)
SEQ ID NO. 1: CelE-CBM1
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC
```

-continued

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

CCCACTCGCCCCAGCGTACCGACCAATACTCCGACTAATACCCCGGCGAA

CACCCTTAAGCCGGGTCCGACCCAGAGCCATTATGGCCAGTGCGGTGGTA

TTGGTTATAGCGGTCCGACCGTGTGCGCAAGCGGTACCACCTGCCAGGTG

CTGAACCCGTATTATAGCCAGTGCCTG

SEQ ID NO. 2: CelE-CBM1
MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTLKPGPTQSHYGQCGGIGYSGPTVCASGTTCQV

LNPYYSQCL

SEQ ID NO. 3: CelE-CBM17
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

-continued

CCCACTCGCCCCAGCGTACCGACCAATACTCCGACTAATACCCCGGCGAA

CACCCTTAAGAGCCAACCGACCGCCCCGAAAGATTTTTCCTCAGGTTTCT

GGGACTTTAACGATGGCACGACCCAGGGTTTCGGCGTGAATCCGGACTCG

CCGATTACGGCAATCAACGTTGAAAATGCTAACAATGCGCTGAAAATTAG

CAACCTGAACAGCAAAGGTAGTAACGATCTGTCCGAAGGCAATTTTTGGG

CCAACGTCCGCATCTCAGCAGACATTTGGGGTCAATCGATCAATATTTAT

GGCGATACCAAACTGACGATGGACGTGATCGCTCCGACCCCGGTTAACGT

CAGCATTGCGGCCATCCCGCAGTCTAGTACGCATGGTTGGGGCAATCCGA

CCCGTGCAATTCGCGTGTGGACGAACAATTTCGTTGCTCAAACCGATGGT

ACGTATAAAGCGACCCTGACGATCTCCACCAACGACTCACCGAATTTTAA

CACCATTGCCACCGATGCAGCCGACTCGGTCGTTACCAATATGATCCTGT

TCGTGGGCTCCAACAGCGATAATATTAGCCTGGACAACATCAAATTTACC

AAATAA

SEQ ID NO. 4: CelE-CBM17
MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTLKSQPTAPKDFSSGFWDFNDGTTQGFGVNPDS

PITAINVENANNALKISNLNSKGSNDLSEGNFWANVRISADIWGQSINIY

GDTKLTMDVIAPTPVNVSIAAIPQSSTHGWGNPTRAIRVWTNNFVAQTDG

TYKATLTISTNDSPNFNTIATDAADSVVTNMILFVGSNSDNISLDNIKFT

K

SEQ ID NO. 5: CelE-CBM3a-41aaLinker
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

-continued

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

CCCACTCGCCCCAGCGTACCGACCAATACTCCGACTAATACCCCGGCGAA

CACCCCAGTAAGCGGTAACCTGAAGGTTGAATTTTATAACTCCAACCCAA

GCGACACAACGAATAGCATCAATCCGCAGTTCAAAGTCACGAACACTGGC

AGTTCAGCTATCGATCTGTCGAAACTGACCCTTCGTTACTACTATACGGT

TGATGGCCAAAAAGATCAGACCTTTTGGTGCGACCATGCAGCAATCATCG

GTAGCAATGGTTCTTATAACGGCATTACTTCTAATGTAAAAGGCACCTTT

GTGAAGATGTCAAGTAGCACCAACAATGCTGATACCTACCTGGAAATTAG

CTTCACGGGTGGCACACTTGAACCAGGAGCCCACGTCCAGATCCAGGGCC

GTTTTGCGAAAAACGATTGGAGCAACTATACGCAATCAAACGATTATAGT

TTCAAAAGCGCGTCTCAATTCGTAGAATGGGATCAGGTGACCGCATATTT

GAACGGAGTGCTGGTTTGGGGGAAAGAACCAGGA

SEQ ID NO. 6: CelE-CBM3a-41aaLinker
MGHHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTPVSGNLKVEFYNSNPSDTTNSINPQFKVTNTG

SSAIDLSKLTLRYYYTVDGQKDQTFWCDHAAIIGSNGSYNGITSNVKGTF

VKMSSSTNNADTYLEISFTGGTLEPGAHVQIQGRFAKNDWSNYTQSNDYS

FKSASQFVEWDQVTAYLNGVLVWGKEPG

SEQ ID NO. 7: CelE-CBM3a-6aaLinker
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

-continued

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

TAAGCGGTAACCTGAAGGTTGAATTTTATAACTCCAACCCAAGCGACACA

ACGAATAGCATCAATCCGCAGTTCAAAGTCACGAACACTGGCAGTTCAGC

TATCGATCTGTCGAAACTGACCCTTCGTTACTACTATACGGTTGATGGCC

AAAAAGATCAGACCTTTTGGTGCGACCATGCAGCAATCATCGGTAGCAAT

GGTTCTTATAACGGCATTACTTCTAATGTAAAAGGCACCTTTGTGAAGAT

GTCAAGTAGCACCAACAATGCTGATACCTACCTGGAAATTAGCTTCACGG

GTGGCACACTTGAACCAGGAGCCCACGTCCAGATCCAGGGCCGTTTTGCG

AAAAACGATTGGAGCAACTATACGCAATCAAACGATTATAGTTTCAAAAG

CGCGTCTCAATTCGTAGAATGGGATCAGGTGACCGCATATTTGAACGGAG

TGCTGGTTTGGGGGAAAGAACCAGGA

SEQ ID NO. 8: CelE-CBM3a-6aaLinker
MGHHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKVSGNLKVEFYNSNPSDT

TNSINPQFKVTNTGSSAIDLSKLTLRYYYTVDGQKDQTFWCDHAAIIGSN

GSYNGITSNVKGTFVKMSSSTNNADTYLEISFTGGTLEPGAHVQIQGRFA

KNDWSNYTQSNDYSFKSASQFVEWDQVTAYLNGVLVWGKEPG

SEQ ID NO. 9: CelE-CBM3a-11aaLinker
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

-continued

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCGTAAGCGGTAACCTGAAGGTTGAATTTTATAACTCC

AACCCAAGCGACACAACGAATAGCATCAATCCGCAGTTCAAAGTCACGAA

CACTGGCAGTTCAGCTATCGATCTGTCGAAACTGACCCTTCGTTACTACT

ATACGGTTGATGGCCAAAAAGATCAGACCTTTTGGTGCGACCATGCAGCA

ATCATCGGTAGCAATGGTTCTTATAACGGCATTACTTCTAATGTAAAAGG

CACCTTTGTGAAGATGTCAAGTAGCACCAACAATGCTGATACCTACCTGG

AAATTAGCTTCACGGGTGGCACACTTGAACCAGGAGCCCACGTCCAGATC

CAGGGCCGTTTTGCGAAAAACGATTGGAGCAACTATACGCAATCAAACGA

TTATAGTTTCAAAAGCGCGTCTCAATTCGTAGAATGGGATCAGGTGACCG

CATATTTGAACGGAGTGCTGGTTTGGGGGAAAGAACCAGGA

SEQ ID NO. 10: CelE-CBM3a-11aaLinker

MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTVSGNLKVEFYNS

NPSDTTNSINPQFKVTNTGSSAIDLSKLTLRYYYTVDGQKDQTFWCDHAA

-continued

IIGSNGSYNGITSNVKGTFVKMSSSTNNADTYLEISFTGGTLEPGAHVQI

QGRFAKNDWSNYTQSNDYSFKSASQFVEWDQVTAYLNGVLVWGKEPG

SEQ ID NO. 11: CelE-CBM3a-21aaLinker

ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGTAAGC

GGTAACCTGAAGGTTGAATTTTATAACTCCAACCCAAGCGACACAACGAA

TAGCATCAATCCGCAGTTCAAAGTCACGAACACTGGCAGTTCAGCTATCG

ATCTGTCGAAACTGACCCTTCGTTACTACTATACGGTTGATGGCCAAAAA

GATCAGACCTTTTGGTGCGACCATGCAGCAATCATCGGTAGCAATGGTTC

TTATAACGGCATTACTTCTAATGTAAAAGGCACCTTTGTGAAGATGTCAA

GTAGCACCAACAATGCTGATACCTACCTGGAAATTAGCTTCACGGGTGGC

ACACTTGAACCAGGAGCCCACGTCCAGATCCAGGGCCGTTTTGCGAAAAA

CGATTGGAGCAACTATACGCAATCAAACGATTATAGTTTCAAAAGCGCGT

CTCAATTCGTAGAATGGGATCAGGTGACCGCATATTTGAACGGAGTGCTG

GTTTGGGGGAAAGAACCAGGA

SEQ ID NO. 12: CelE-CBM3a-21aaLinker

MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

-continued

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTNTATPTKSATVS

GNLKVEFYNSNPSDTTNSINPQFKVTNTGSSAIDLSKLTLRYYYTVDGQK

DQTFWCDHAAIIGSNGSYNGITSNVKGTFVKMSSSTNNADTYLEISFTGG

TLEPGAHVQIQGRFAKNDWSNYTQSNDYSFKSASQFVEWDQVTAYLNGVL

VWGKEPG

SEQ ID NO. 13: CelE-CBM3a-31aaLinker
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGAATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

CCCACTCGCCCCAGCGTACCGACCGTAAGCGGTAACCTGAAGGTTGAATT

TTATAACTCCAACCCAAGCGACACAACGAATAGCATCAATCCGCAGTTCA

AAGTCACGAACACTGGCAGTTCAGCTATCGATCTGTCGAAACTGACCCTT

CGTTACTACTATACGGTTGATGGCCAAAAAGATCAGACCTTTTGGTGCGA

CCATGCAGCAATCATCGGTAGCAATGGTTCTTATAACGGCATTACTTCTA

ATGTAAAAGGCACCTTTGTGAAGATGTCAAGTAGCACCAACAATGCTGAT

ACCTACCTGGAAATTAGCTTCACGGGTGGCACACTTGAACCAGGAGCCCA

CGTCCAGATCCAGGGCCGTTTTGCGAAAAACGATTGGAGCAACTATACGC

-continued

AATCAAACGATTATAGTTTCAAAAGCGCGTCTCAATTCGTAGAATGGGAT

CAGGTGACCGCATATTTGAACGGAGTGCTGGTTTGGGGGAAAGAACCAGG

A

SEQ ID NO. 14: CelE-CBM3a-31aaLinker
MGHHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGEFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTVSGNLKVEFYNSNPSDTTNSINPQFKVTNTGSSAIDLSKLTL

RYYYTVDGQKDQTFWCDHAAIIGSNGSYNGITSNVKGTFVKMSSSTNNAD

TYLEISFTGGTLEPGAHVQIQGRFAKNDWSNYTQSNDYSFKSASQFVEWD

QVTAYLNGVLVWGKEPG

Mutant sequences (catalytic nucleophile residue mutated to increase transglycosylation activity):
SEQ ID NO. 15: CelE-CBM1-E316G
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGGATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

-continued

CCCACTCGCCCCAGCGTACCGACCAATACTCCGACTAATACCCCGGCGAA

CACCCTTAAGCCGGGTCCGACCCAGAGCCATTATGGCCAGTGCGGTGGTA

TTGGTTATAGCGGTCCGACCGTGTGCGCAAGCGGTACCACCTGCCAGGTG

CTGAACCCGTATTATAGCCAGTGCCTG

SEQ ID NO. 16: CelE-CBM1-E316G
MGHHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGGFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTLKPGPTQSHYGQCGGIGYSGPTVCASGTTCQV

LNPYYSQCL

SEQ ID NO. 17: CelE-CBM17-E316G
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGGATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

CCCACTCGCCCCAGCGTACCGACCAATACTCCGACTAATACCCCGGCGAA

CACCCTTAAGAGCCAACCGACCGCCCCGAAAGATTTTTCCTCAGGTTTCT

-continued

GGGACTTTAACGATGGCACGACCCAGGGTTTCGGCGTGAATCCGGACTCG

CCGATTACGGCAATCAACGTTGAAAATGCTAACAATGCGCTGAAAATTAG

CAACCTGAACAGCAAAGGTAGTAACGATCTGTCCGAAGGCAATTTTTGGG

CCAACGTCCGCATCTCAGCAGACATTTGGGGTCAATCGATCAATATTTAT

GGCGATACCAAACTGACGATGGACGTGATCGCTCCGACCCCGGTTAACGT

CAGCATTGCGGCCATCCCGCAGTCTAGTACGCATGGTTGGGGCAATCCGA

CCCGTGCAATTCGCGTGTGGACGAACAATTTCGTTGCTCAAACCGATGGT

ACGTATAAAGCGACCCTGACGATCTCCACCAACGACTCACCGAATTTTAA

CACCATTGCCACCGATGCAGCCGACTCGGTCGTTACCAATATGATCCTGT

TCGTGGGCTCCAACAGCGATAATATTAGCCTGGACAACATCAAATTTACC

AAATAA

SEQ ID NO. 18: CelE-CBM17-E316G
MGHHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGGFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTLKSQPTAPKDFSSGFWDFNDGTTQGFGVNPDS

PITAINVENANNALKISNLNSKGSNDLSEGNFWANVRISADIWGQSINIY

GDTKLTMDVIAPTPVNVSIAAIPQSSTHGWGNPTRAIRVWTNNFVAQTDG

TYKATLTISTNDSPNFNTIATDAADSVVTNMILFVGSNSDNISLDNIKFT

K

SEQ ID NO. 19: CelE-CBM3a-E316G-41aaLinker
ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

-continued

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGGATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

GTGCCACTCCTACCAATACGGCGACTCCGACTAAGTCGGCAACGGCAACG

CCCACTCGCCCCAGCGTACCGACCAATACTCCGACTAATACCCCGGCGAA

CACCCCAGTAAGCGGTAACCTGAAGGTTGAATTTTATAACTCCAACCCAA

GCGACACAACGAATAGCATCAATCCGCAGTTCAAAGTCACGAACACTGGC

AGTTCAGCTATCGATCTGTCGAAACTGACCCTTCGTTACTACTATACGGT

TGATGGCCAAAAAGATCAGACCTTTTGGTGCGACCATGCAGCAATCATCG

GTAGCAATGGTTCTTATAACGGCATTACTTCTAATGTAAAAGGCACCTTT

GTGAAGATGTCAAGTAGCACCAACAATGCTGATACCTACCTGGAAATTAG

CTTCACGGGTGGCACACTTGAACCAGGAGCCCACGTCCAGATCCAGGGCC

GTTTTGCGAAAAACGATTGGAGCAACTATACGCAATCAAACGATTATAGT

TTCAAAAGCGCGTCTCAATTCGTAGAATGGGATCAGGTGACCGCATATTT

GAACGGAGTGCTGGTTTGGGGGAAAGAACCAGGA

SEQ ID NO. 20: CelE-CBM3a-E316G-41aaLinker

MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGGFGTIDKNNLSSRVAHAEHYAREAVSRGIAVFWWDNGYYNPGDAETYA

LLNRRNLTWYYPEIVQALMRGAGVEGLNATPTKGATPTNTATPTKSATAT

PTRPSVPTNTPTNTPANTPVSGNLKVEFYNSNPSDTTNSINPQFKVTNTG

SSAIDLSKLTLRYYYTVDGQKDQTFWCDHAAIIGSNGSYNGITSNVKGTF

VKMSSSTNNADTYLEISFTGGTLEPGAHVQIQGRFAKNDWSNYTQSNDYS

FKSASQFVEWDQVTAYLNGVLVWGKEPG

SEQ ID NO. 21: CelE-CBM3a-E316G-6aaLinker

ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

AAATGGGCTTTAATGCCGTCAGAGTGCCTGTTACCTGGGATACACACATC

GGACCTGCTCCGGACTATAAAATTGACGAAGCATGGCTGAACAGAGTTGA

GGAAGTGGTAAACTATGTTCTTGACTGCGGTATGTATGCCATCATAAATG

TTCACCATGACAATACATGGATTATACCTACATATGCCAATGAGCAAAGG

-continued

AGTAAAGAAAAACTTGTAAAAGTTTGGGAACAAATAGCAACCCGTTTTAA

AGATTATGACGACCATTTGTTGTTTGAGACAATGAACGAACCGAGAGAAG

TAGGTTCACCTATGGAATGGATGGGCGGAACGTATGAAAACCGAGATGTG

ATAAACAGATTTAATTTGGCGGTTGTTAATACCATCAGAGCAAGCGGCGG

AAATAACGATAAAAGATTCATACTGGTTCCGACCAATGCGGCAACCGGCC

TGGATGTTGCATTAAACGACCTTGTCATTCCGAACAATGACAGCAGAGTA

ATAGTATCCATACATGCTTATTCACCGTATTTCTTTGCTATGGATGTCAA

CGGAACTTCATATTGGGGAAGTGACTATGACAAGGCTTCTTTTACAAGTG

AACTTGATGCTATTTACAACAGATTTGTGAAAAACGGAAGGGCTGTAATT

ATCGGAGGATTCGGAACCATTGACAAGAACAACCTGTCTTCAAGGGTGGC

TCATGCCGAGCACTATGCAAGAGAAGCAGTTTCAAGAGGAATTGCTGTTT

TCTGGTGGGATAACGGCTATTACAATCCGGGTGATGCAGAAACTTATGCA

TTGCTGAACAGAAGAAATCTTACATGGTATTATCCTGAAATTGTCCAGGC

TCTTATGAGAGGTGCCGGCGTTGAAGGTTTAAACGCGACTCCCACTAAAG

TAAGCGGTAACCTGAAGGTTGAATTTTATAACTCCAACCCAAGCGACACA

ACGAATAGCATCAATCCGCAGTTCAAAGTCACGAACACTGGCAGTTCAGC

TATCGATCTGTCGAAACTGACCCTTCGTTACTACTATACGGTTGATGGCC

AAAAAGATCAGACCTTTTGGTGCGACCATGCAGCAATCATCGGTAGCAAT

GGTTCTTATAACGGCATTACTTCTAATGTAAAAGGCACCTTTGTGAAGAT

GTCAAGTAGCACCAACAATGCTGATACCTACCTGGAAATTAGCTTCACGG

GTGGCACACTTGAACCAGGAGCCCACGTCCAGATCCAGGGCCGTTTTGCG

AAAAACGATTGGAGCAACTATACGCAATCAAACGATTATAGTTTCAAAAG

CGCGTCTCAATTCGTAGAATGGGATCAGGTGACCGCATATTTGAACGGAG

TGCTGGTTTGGGGGAAAGAACCAGGA

SEQ ID NO. 22: CelE-CBM3a-E316G-6aaLinker

MGHHHHHHHHASENLYFQAIAMGTKLLDASGNELVMRGMRDISAIDLVKE

IKIGWNLGNTLDAPTETAWGNPRTTKAMIEKVREMGFNAVRVPVTWDTHI

GPAPDYKIDEAWLNRVEEVVNYVLDCGMYAIINVHHDNTWIIPTYANEQR

SKEKLVKVWEQIATRFKDYDDHLLFETMNEPREVGSPMEWMGGTYENRDV

INRFNLAVVNTIRASGGNNDKRFILVPTNAATGLDVALNDLVIPNNDSRV

IVSIHAYSPYFFAMDVNGTSYWGSDYDKASFTSELDAIYNRFVKNGRAVI

IGGFGTIDKNNLSSRVAHAEHYAREAVSRGIAVFWWDNGYYNPGDAETYA

LLNRRNLTWYYPEIVQALMRGAGVEGLNATPTKVSGNLKVEFYNSNPSDT

TNSINPQFKVTNTGSSAIDLSKLTLRYYYTVDGQKDQTFWCDHAAIIGSN

GSYNGITSNVKGTFVKMSSSTNNADTYLEISFTGGTLEPGAHVQIQGRFA

KNDWSNYTQSNDYSFKSASQFVEWDQVTAYLNGVLVWGKEPG

SEQ ID NO. 23: CelE-CBM3a-E316G-11aaLinker

ATGGGACATCACCATCATCACCATCACCATGCATCCGAAAACCTGTACTT

CCAGGCGATCGCCATGGGAACAAAGCTTTTGGATGCAAGCGGAAACGAGC

TTGTAATGAGGGGCATGCGTGATATTTCAGCAATAGATTTGGTTAAAGAA

ATAAAAATCGGATGGAATTTGGGAAATACTTTGGATGCTCCTACAGAGAC

TGCCTGGGGAAATCCAAGGACAACCAAGGCAATGATAGAAAAGGTAAGGG

-continued

AAATGGGCTTTAATGCCGTCAGAGTGCCTGTTACCTGGGATACACACATC
GGACCTGCTCCGGACTATAAAATTGACGAAGCATGGCTGAACAGAGTTGA
GGAAGTGGTAAACTATGTTCTTGACTGCGGTATGTATGCCATCATAAATG
TTCACCATGACAATACATGGATTATACCTACATATGCCAATGAGCAAAGG
AGTAAAGAAAAACTTGTAAAAGTTTGGGAACAAATAGCAACCCGTTTTAA
AGATTATGACGACCATTTGTTGTTTGAGACAATGAACGAACCGAGAGAAG
TAGGTTCACCTATGGAATGGATGGGCGGAACGTATGAAAACCGAGATGTG
ATAAACAGATTTAATTTGGCGGTTGTTAATACCATCAGAGCAAGCGGCGG
AAATAACGATAAAAGATTCATACTGGTTCCGACCAATGCGGCAACCGGCC
TGGATGTTGCATTAAACGACCTTGTCATTCCGAACAATGACAGCAGAGTA
ATAGTATCCATACATGCTTATTCACCGTATTTCTTTGCTATGGATGTCAA
CGGAACTTCATATTGGGGAAGTGACTATGACAAGGCTTCTTTTACAAGTG
AACTTGATGCTATTTACAACAGATTTGTGAAAAACGGAAGGGCTGTAATT
ATCGGAGGATTCGGAACCATTGACAAGAACAACCTGTCTTCAAGGGTGGC
TCATGCCGAGCACTATGCAAGAGAAGCAGTTTCAAGAGGAATTGCTGTTT
TCTGGTGGGATAACGGCTATTACAATCCGGGTGATGCAGAAACTTATGCA
TTGCTGAACAGAAGAAATCTTACATGGTATTATCCTGAAATTGTCCAGGC
TCTTATGAGAGGTGCCGGCGTTGAAGGTTTAAACGCGACTCCCACTAAAG
GTGCCACTCCTACCGTAAGCGGTAACCTGAAGGTTGAATTTTATAACTCC
AACCCAAGCGACACAACGAATAGCATCAATCCGCAGTTCAAAGTCACGAA
CACTGGCAGTTCAGCTATCGATCTGTCGAAACTGACCCTTCGTTACTACT
ATACGGTTGATGGCCAAAAAGATCAGACCTTTTGGTGCGACCATGCAGCA
ATCATCGGTAGCAATGGTTCTTATAACGGCATTACTTCTAATGTAAAAGG
CACCTTTGTGAAGATGTCAAGTAGCACCAACAATGCTGATACCTACCTGG
AAATTAGCTTCACGGGTGGCACACTTGAACCAGGAGCCCACGTCCAGATC
CAGGGCCGTTTTGCGAAAAACGATTGGAGCAACTATACGCAATCAAACGA
TTATAGTTTCAAAAGCGCGTCTCAATTCGTAGAATGGGATCAGGTGACCG
CATATTTGAACGGAGTGCTGGTTTGGGGGAAAGAACCAGGA

SEQ ID NO. 24: CelE-CBM3a-E316G-11aaLinker
MGHHHHHHHHHASENLYFQAIAMGTKLLDASGNELVMRGMRDISAIDLVKE
IKIGWNLGNTLDAPTETAWGNPRTTKAMIEKVREMGFNAVRVPVTWDTHI
GPAPDYKIDEAWLNRVEEVVNYVLDCGMYAIINVHHDNTWIIPTYANEQR
SKEKLVKVWEQIATRFKDYDDHLLFETMNEPREVGSPMEWMGGTYENRDV
INRFNLAVVNTIRASGGNNDKRFILVPTNAATGLDVALNDLVIPNNDSRV
IVSIHAYSPYFFAMDVNGTSYWGSDYDKASFTSELDAIYNRFVKNGRAVI
IGGFGTIDKNNLSSRVAHAEHYAREAVSRGIAVFWWDNGYYNPGDAETYA
LLNRRNLTWYYPEIVQALMRGAGVEGLNATPTKGATPTVSGNLKVEFYNS
NPSDTTNSINPQFKVTNTGSSAIDLSKLTLRYYYTVDGQKDQTFWCDHAA
IIGSNGSYNGITSNVKGTFVKMSSSTNNADTYLEISFTGGTLEPGAHVQI
QGRFAKNDWSNYTQSNDYSFKSASQFVEWDQVTAYLNGVLVWGKEPG -continued SEQ ID NO. 25: CelE-CBM3a-E316G-21aaLinker
ATGGGACATCACCATCATCACCATCACCATGCATCCGAAAACCTGTACTT
CCAGGCGATCGCCATGGGAACAAAGCTTTTGGATGCAAGCGGAAACGAGC
TTGTAATGAGGGGCATGCGTGATATTTCAGCAATAGATTTGGTTAAAGAA
ATAAAAATCGGATGGAATTTGGGAAATACTTTGGATGCTCCTACAGAGAC
TGCCTGGGGAAATCCAAGGACAACCAAGGCAATGATAGAAAAGGTAAGGG
AAATGGGCTTTAATGCCGTCAGAGTGCCTGTTACCTGGGATACACACATC
GGACCTGCTCCGGACTATAAAATTGACGAAGCATGGCTGAACAGAGTTGA
GGAAGTGGTAAACTATGTTCTTGACTGCGGTATGTATGCCATCATAAATG
TTCACCATGACAATACATGGATTATACCTACATATGCCAATGAGCAAAGG
AGTAAAGAAAAACTTGTAAAAGTTTGGGAACAAATAGCAACCCGTTTTAA
AGATTATGACGACCATTTGTTGTTTGAGACAATGAACGAACCGAGAGAAG
TAGGTTCACCTATGGAATGGATGGGCGGAACGTATGAAAACCGAGATGTG
ATAAACAGATTTAATTTGGCGGTTGTTAATACCATCAGAGCAAGCGGCGG
AAATAACGATAAAAGATTCATACTGGTTCCGACCAATGCGGCAACCGGCC
TGGATGTTGCATTAAACGACCTTGTCATTCCGAACAATGACAGCAGAGTA
ATAGTATCCATACATGCTTATTCACCGTATTTCTTTGCTATGGATGTCAA
CGGAACTTCATATTGGGGAAGTGACTATGACAAGGCTTCTTTTACAAGTG
AACTTGATGCTATTTACAACAGATTTGTGAAAAACGGAAGGGCTGTAATT
ATCGGAGGATTCGGAACCATTGACAAGAACAACCTGTCTTCAAGGGTGGC
TCATGCCGAGCACTATGCAAGAGAAGCAGTTTCAAGAGGAATTGCTGTTT
TCTGGTGGGATAACGGCTATTACAATCCGGGTGATGCAGAAACTTATGCA
TTGCTGAACAGAAGAAATCTTACATGGTATTATCCTGAAATTGTCCAGGC
TCTTATGAGAGGTGCCGGCGTTGAAGGTTTAAACGCGACTCCCACTAAAG
GTGCCACTCCTACCAATACGGCGACTCCGACTAAGTCGGCAACGGTAAGC
GGTAACCTGAAGGTTGAATTTTATAACTCCAACCCAAGCGACACAACGAA
TAGCATCAATCCGCAGTTCAAAGTCACGAACACTGGCAGTTCAGCTATCG
ATCTGTCGAAACTGACCCTTCGTTACTACTATACGGTTGATGGCCAAAAA
GATCAGACCTTTTGGTGCGACCATGCAGCAATCATCGGTAGCAATGGTTC
TTATAACGGCATTACTTCTAATGTAAAAGGCACCTTTGTGAAGATGTCAA
GTAGCACCAACAATGCTGATACCTACCTGGAAATTAGCTTCACGGGTGGC
ACACTTGAACCAGGAGCCCACGTCCAGATCCAGGGCCGTTTTGCGAAAAA
CGATTGGAGCAACTATACGCAATCAAACGATTATAGTTTCAAAAGCGCGT
CTCAATTCGTAGAATGGGATCAGGTGACCGCATATTTGAACGGAGTGCTG
GTTTGGGGGAAAGAACCAGGA SEQ ID NO. 26: CelE-CBM3a-E316G-21aaLinker
MGHHHHHHHHHASENLYFQAIAMGTKLLDASGNELVMRGMRDISAIDLVKE
IKIGWNLGNTLDAPTETAWGNPRTTKAMIEKVREMGFNAVRVPVTWDTHI
GPAPDYKIDEAWLNRVEEVVNYVLDCGMYAIINVHHDNTWIIPTYANEQR
SKEKLVKVWEQIATRFKDYDDHLLFETMNEPREVGSPMEWMGGTYENRDV
INRFNLAVVNTIRASGGNNDKRFILVPTNAATGLDVALNDLVIPNNDSRV
IVSIHAYSPYFFAMDVNGTSYWGSDYDKASFTSELDAIYNRFVKNGRAVI IGGFGTIDKNNLSSRVAHAEHYAREAVSRGIAVFWWDNGYYNPGDAETYA
LLNRRNLTWYYPEIVQALMRGAGVEGLNATPTKGATPTNTATPTKSATVS
GNLKVEFYNSNPSDTTNSINPQFKVTNTGSSAIDLSKLTLRYYYTVDGQK
DQTFWCDHAAIIGSNGSYNGITSNVKGTFVKMSSSTNNADTYLEISFTGG
TLEPGAHVQIQGRFAKNDWSNYTQSNDYSFKSASQFVEWDQVTAYLNGVL
VWGKEPG SEQ ID NO. 27: CelE-CBM3a-E316G-31aaLinker
ATGGGACATCACCATCATCACCATCACCATGCATCCGAAAACCTGTACTT
CCAGGCGATCGCCATGGGAACAAAGCTTTTGGATGCAAGCGGAAACGAGC
TTGTAATGAGGGGCATGCGTGATATTTCAGCAATAGATTTGGTTAAAGAA
ATAAAAATCGGATGGAATTTGGGAAATACTTTGGATGCTCCTACAGAGAC
TGCCTGGGGAAATCCAAGGACAACCAAGGCAATGATAGAAAAGGTAAGGG
AAATGGGCTTTAATGCCGTCAGAGTGCCTGTTACCTGGGATACACACATC
GGACCTGCTCCGGACTATAAAATTGACGAAGCATGGCTGAACAGAGTTGA
GGAAGTGGTAAACTATGTTCTTGACTGCGGTATGTATGCCATCATAAATG
TTCACCATGACAATACATGGATTATACCTACATATGCCAATGAGCAAAGG
AGTAAAGAAAAACTTGTAAAAGTTTGGGAACAAATAGCAACCCGTTTTAA
AGATTATGACGACCATTTGTTGTTTGAGACAATGAACGAACCGAGAGAAG
TAGGTTCACCTATGGAATGGATGGGCGGAACGTATGAAAACCGAGATGTG
ATAAACAGATTTAATTTGGCGGTTGTTAATACCATCAGAGCAAGCGGCGG
AAATAACGATAAAAGATTCATACTGGTTCCGACCAATGCGGCAACCGGCC
TGGATGTTGCATTAAACGACCTTGTCATTCCGAACAATGACAGCAGAGTA
ATAGTATCCATACATGCTTATTCACCGTATTTCTTTGCTATGGATGTCAA
CGGAACTTCATATTGGGGAAGTGACTATGACAAGGCTTCTTTTACAAGTG
AACTTGATGCTATTTACAACAGATTTGTGAAAAACGGAAGGGCTGTAATT
ATCGGAGGATTCGGAACCATTGACAAGAACAACCTGTCTTCAAGGGTGGC
TCATGCCGAGCACTATGCAAGAGAAGCAGTTTCAAGAGGAATTGCTGTTT
TCTGGTGGGATAACGGCTATTACAATCCGGGTGATGCAGAAACTTATGCA
TTGCTGAACAGAAGAAATCTTACATGGTATTATCCTGAAATTGTCCAGGC
TCTTATGAGAGGTGCCGGCGTTGAAGGTTTAAACGCGACTCCCACTAAAG
GTGCCACTCCTACCAATACGGCGACTCCGACTAAGTCGGCAACGGCAACG
CCCACTCGCCCCAGCGTACCGACCGTAAGCGGTAACCTGAAGGTTGAATT
TTATAACTCCAACCCAAGCGACACAACGAATAGCATCAATCCGCAGTTCA
AAGTCACGAACACTGGCAGTTCAGCTATCGATCTGTCGAAACTGACCCTT
CGTTACTACTATACGGTTGATGGCCAAAAAGATCAGACCTTTTGGTGCGA
CCATGCAGCAATCATCGGTAGCAATGGTTCTTATAACGGCATTACTTCTA
ATGTAAAAGGCACCTTTGTGAAGATGTCAAGTAGCACCAACAATGCTGAT
ACCTACCTGGAAATTAGCTTCACGGGTGGCACACTTGAACCAGGAGCCCA
CGTCCAGATCCAGGGCCGTTTTGCGAAAAACGATTGGAGCAACTATACGC
AATCAAACGATTATAGTTTCAAAAGCGCGTCTCAATTCGTAGAATGGGAT
CAGGTGACCGCATATTTGAACGGAGTGCTGGTTTGGGGGAAAGAACCAGG
A SEQ ID NO. 28: CelE-CBM3a-E316G-31aaLinker
MGHHHHHHHHASENLYFQAIAMGTKLLDASGNELVMRGMRDISAIDLVKE
IKIGWNLGNTLDAPTETAWGNPRTTKAMIEKVREMGFNAVRVPVTWDTHI
GPAPDYKIDEAWLNRVEEVVNYVLDCGMYAIINVHHDNTWIIPTYANEQR
SKEKLVKVWEQIATRFKDYDDHLLFETMNEPREVGSPMEWMGGTYENRDV
INRFNLAVVNTIRASGGNNDKRFILVPTNAATGLDVALNDLVIPNNDSRV
IVSIHAYSPYFFAMDVNGTSYWGSDYDKASFTSELDAIYNRFVKNGRAVI
IGGFGTIDKNNLSSRVAHAEHYAREAVSRGIAVFWWDNGYYNPGDAETYA
LLNRRNLTWYYPEIVQALMRGAGVEGLNATPTKGATPTNTATPTKSATAT
PTRPSVPTVSGNLKVEFYNSNPSDTTNSINPQFKVTNTGSSAIDLSKLTL
RYYYTVDGQKDQTFWCDHAAIIGSNGSYNGITSNVKGTFVKMSSSTNNAD
TYLEISFTGGTLEPGAHVQIQGRFAKNDWSNYTQSNDYSFKSASQFVEWD
QVTAYLNGVLVWGKEPG SEQ ID NO. 29: GH5_g5_E310S_CBM3a
MGMGATNLTAAQIQRGMGLGFNIGNTFDSSNNDMGCLVSNHELHWGNPAV
TQAYVDAIYDKGFRSIRLPITWYEFITEDNGTYSIKPEYLARVKEVVDYA
YNKNMYVIINVHHENWINRSDLAASYNSISPKLKGVWKVIAEYFSDYDQR
LIFEGMNEPRLVGVEGVEWVGNAEAYNVVNKLDKDFISTVRSVASPYKST
RLLMVPSYAASVNPVAYEKMDMTMFNDPYVAASIHAYSPYNFAMGNGDHS
DFSPYKAELESIFAGLRTTFTSKKIPVILGSFSSSNFNNQSARVAWAKCY
MEQAKKLGIPCVLWDNDVIAMQDDGEAHGYLNRATNKWYSESEPVVNALL
STLNDVLNATPTKGATPTNTATPTKSATATPTRPSVPTNTPTNTPANTPV
SGNLKVEFYNSNPSDTTNSINPQFKVTNTGSSAIDLSKLTLRYYYTVDGQ
KDQTFWCDHAAIIGSNGSYNGITSNVKGTFVKMSSSTNNADTYLEISFTG
GTLEPGAHVQIQGRFAKNDWSNYTQSNDYSFKSASQFVEWDQVTAYLNGV
LVWGKEPG SEQ ID NO. 30: GH5_gl0_E313G_CBM3a
MPAKTVYAAGTDKTATEVVSDMTVGWNLGNSLDSYGQSSNFPYTSSNETY
WGNPKTTKALIDAVAEAGFNTIRIPVSWGQYTTGSDYQIPDFFMSRVKEV
VDYAIANDMYVILNTHHDINSDYCFYVPNNANKDRSEKYFNSIWTQVANE
FKNYDYHLVFETMNEPRLVGHSEEWWFPRNNPSSDIKEAVACINDYNQVA
LDAIRATGGNNATRCVMVPGYDASIEGCMTDGFKMPKDSASNRLILSVHA
YIPYTFALASDTYTKTFSDNLKGDIDSFFNDLDSKFLSKNIPVVVGGTSA
TNRNNKDERVKWADYYWGAAAKHSNVAMVLWDNNVYENNSAGSNGECHMY
IDRNSLQWKDPEIISAIMKVLNATPTKGATPTNTATPTKSATATPTRPSV
PTNTPTNTPANTPVSGNLKVEFYNSNPSDTTNSINPQFKVTNTGSSAIDL
SKLTLRYYYTVDGQKDQTFWCDHAAIIGSNGSYNGITSNVKGTFVKMSSS
TNNADTYLEISFTGGTLEPGAHVQIQGRFAKNDWSNYTQSNDYSFKSASQ
FVEWDQVTAYLNGVLVWGKEPG Example 1

The effect of each CBM on the transglycosylation activity of CelE was tested by reacting 2 nanomoles of each construct with 10 mM of pNP-Cellobiose. The reaction conditions were 60° C., pH 6.5 and an RPM of 350. The reaction was stopped after 7 hours by freezing the samples at −20° C. The results of these reactions are as follows.

Figure 3A:
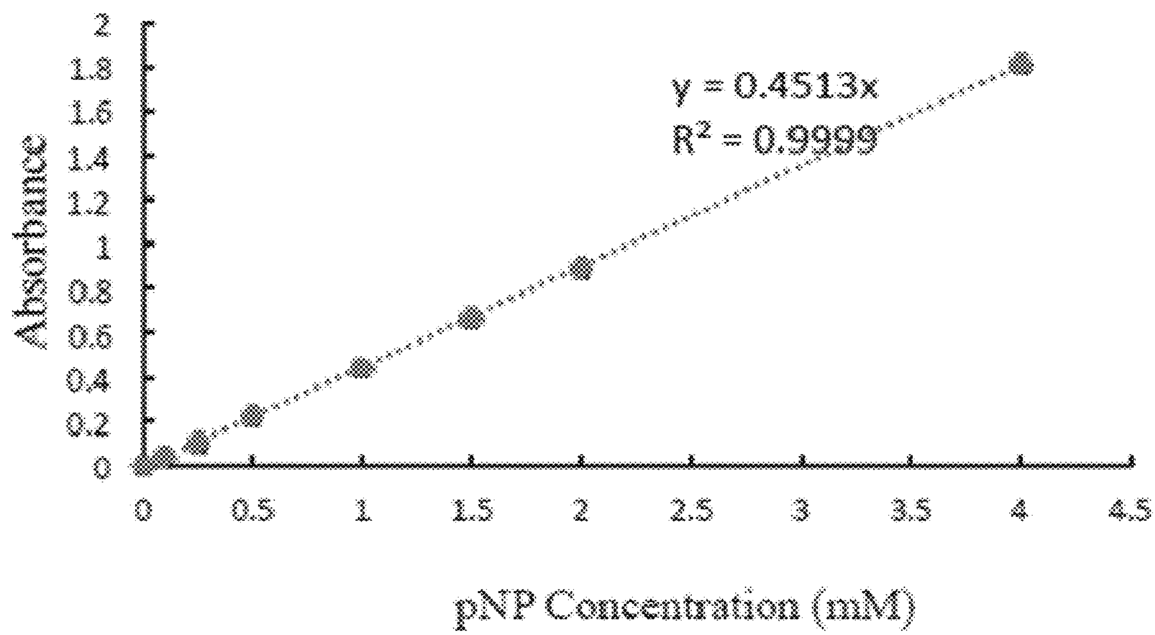
FIG. 3A illustrates a pNP standard curve produced by diluting a pNP solution of known concentrations.
Figure 3B:
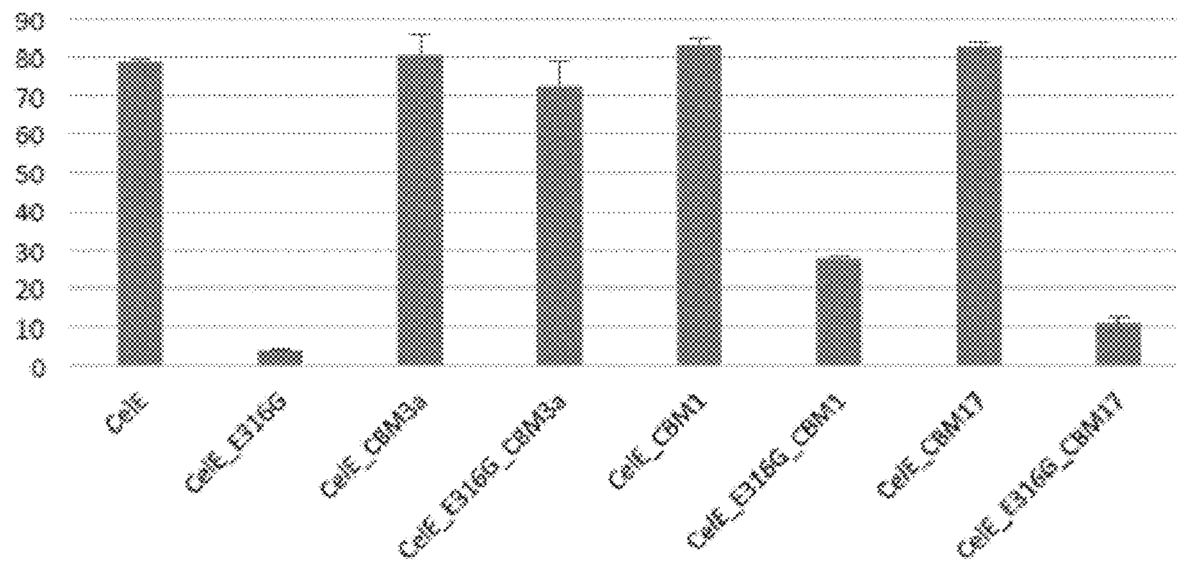
FIG. 3B illustrates % conversion of pNP-Cellobiose for each protein after reacting for 7 hours at 60° C. and 350 RPM.

The products of the pNP-Cellobiose reactions were analyzed in two different ways. First, the pNP-C conversion was measured by measuring the pNP absorbance of each sample. The pNP absorbance was measured by mixing 10 μL of sample with 90 μL of deionized water and 100 μL of 0.1 M NaOH and the comparing that value to the standard curve produced by pNP samples of known concentration. The standard curve of the pNP samples and the pNP-Cellobiose conversion can be seen below in FIGS. 3*a* and 3*b*, respectively.

The samples with the highest percent conversion of pNP-Cellobiose showed the higher activity. These results show that CBMs can have a positive effect on increasing the activity of the CelE nucleophilic mutant towards wither hydrolysis or promote transglycosylation.

Figure 4:
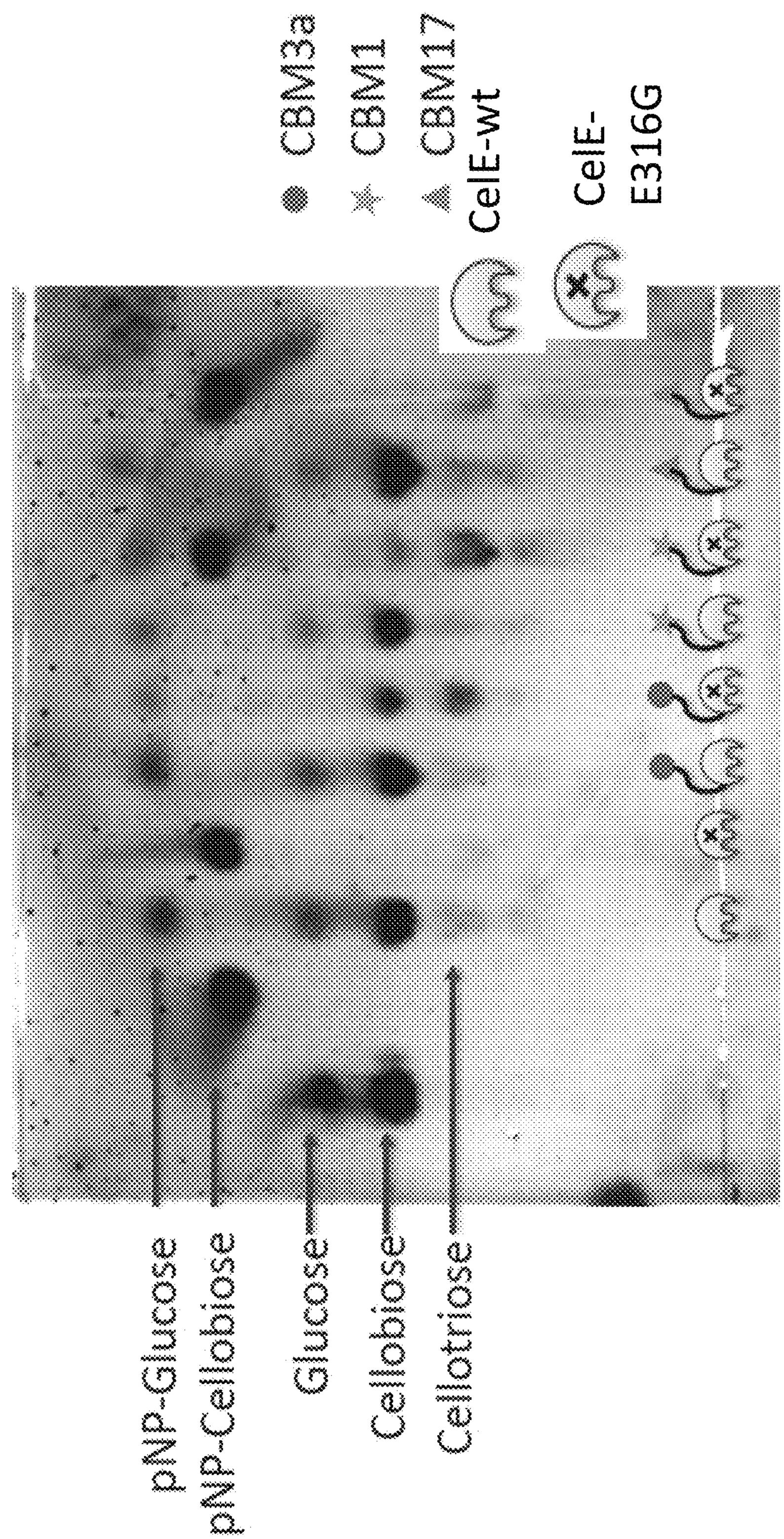
FIG. 4 illustrates a carbohydrate stained TLC analysis of the 7 hour reaction samples. Each column represents the composition of each reaction mixture, with different enzymes.

The next type of analysis of the sample was a thinned liquid chromatography (TLC) analysis which is used to analyze the specific types of products produced by the reactions of each protein with pNP-Cellobiose. An image of the carbohydrate stained TLC plate can be seen in FIG. 4.

Figure 5:
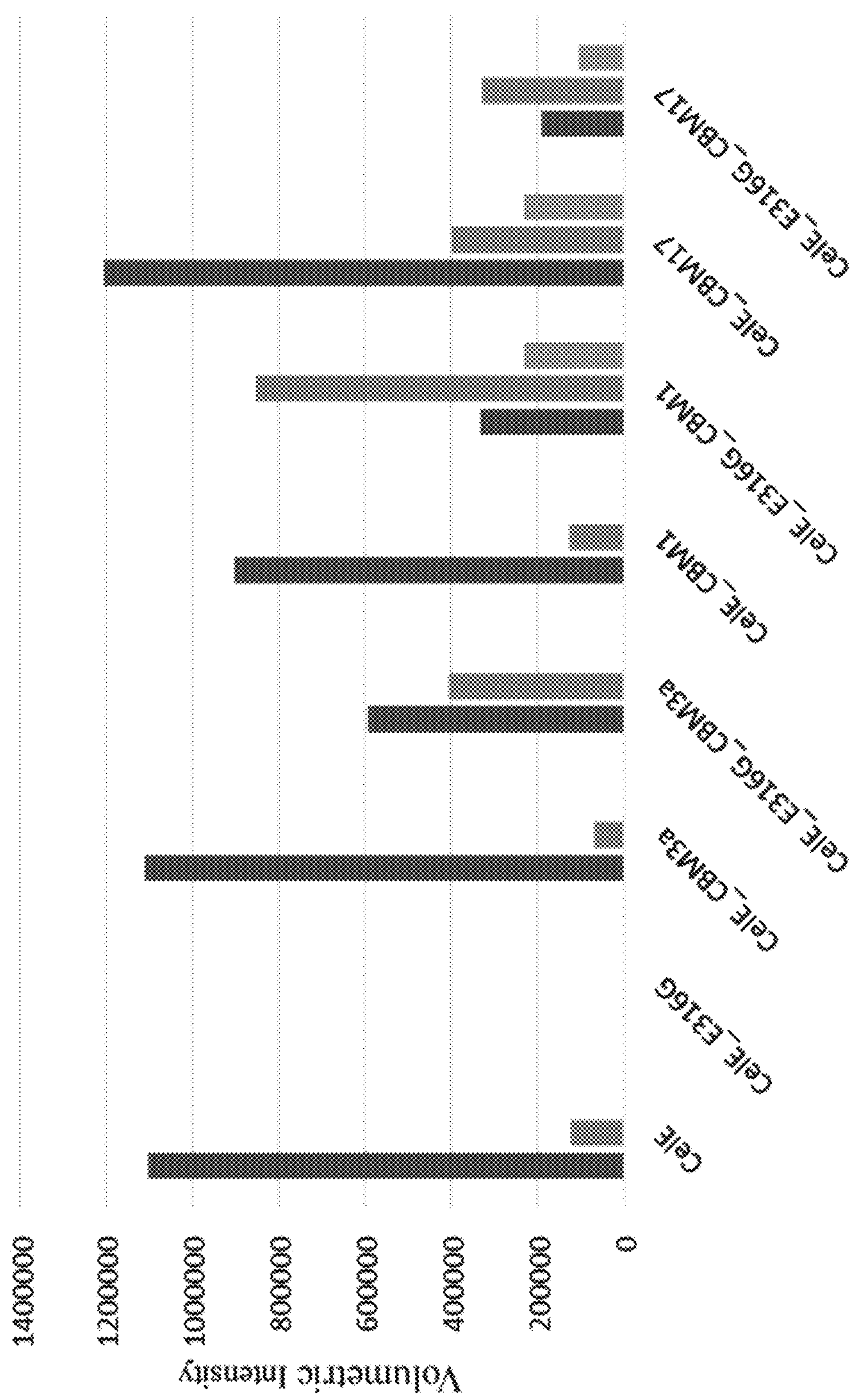
FIG. 5 illustrates volumetric intensity of cellobiose shown as the blue bar, unknown transglycosylation product 1 shown as the orange bar, and unknown transglycosylation product shown as the grey bar.
Figure 6:
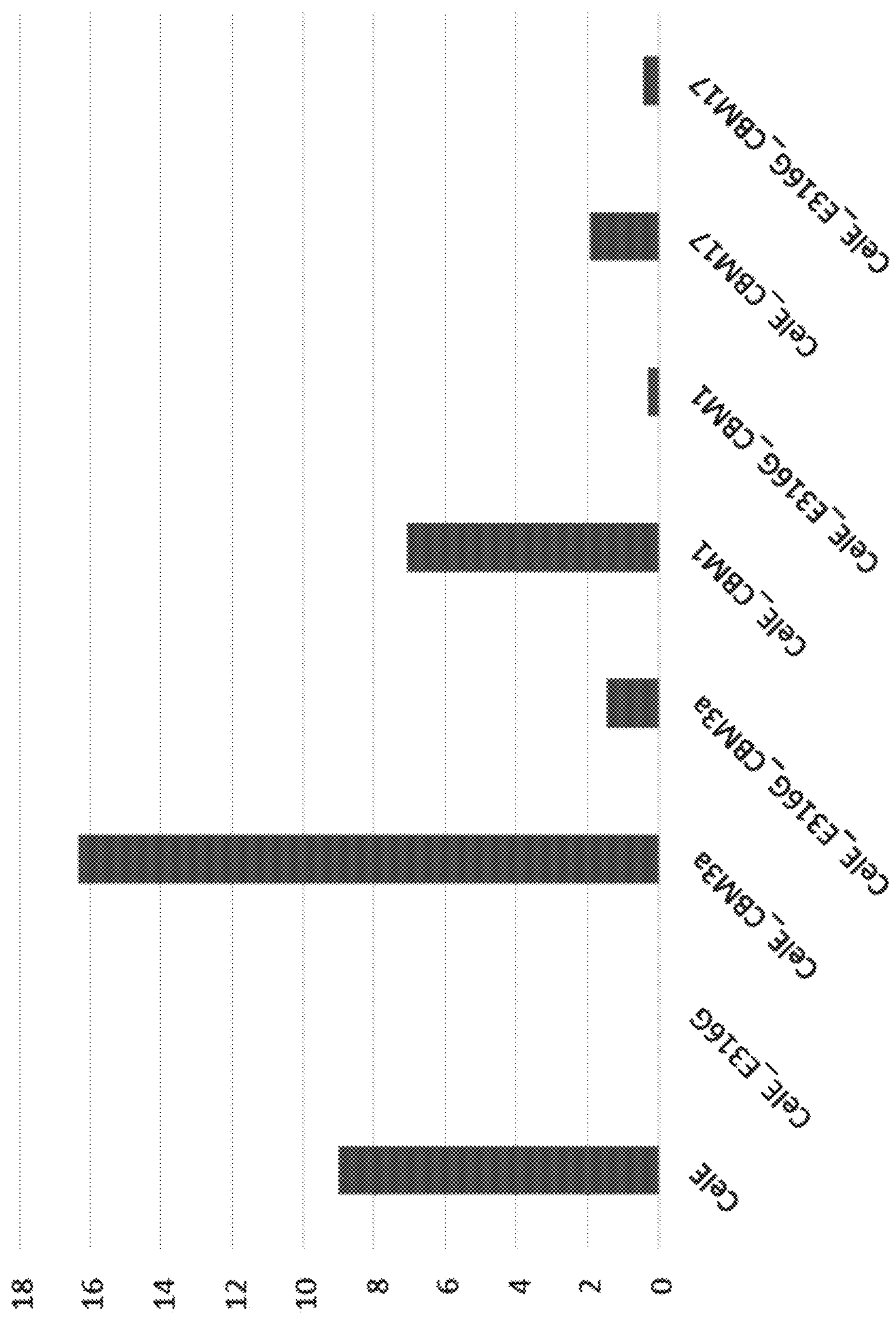
FIG. 6 illustrates H/T ratios for certain proteins of the invention, which were measured using semi-quantitative volumetric analysis.

After producing this image of the stained TLC plate, volumetric analysis was done to show which protein favors a transglycosylation pathway or hydrolysis pathway. The H/T ratio is measured by taking the volumetric intensity of the cellobiose as the intensity of the hydrolysis products and then dividing that by the intensity of the other products, which most likely consists of cellotriose or cellotetraose. The volumetric intensity of each product and H/T ratios for each protein can be seen below in FIGS. 5 and 6, respectively.

The H/T ratios show that the CelE nucleophilic mutant protein is inactive on pNP-C but, the addition of a CBM as a positive impact on the activity of the mutant. The CelE nucleophilic mutant protein amended to a CBM show a very low H/T ratio. This shows the CBMs have a positive impact on the transglycosylation activity of CelE nucleophilic mutant proteins and CBM3a shows the highest transglycosylation activity.

Example 2

The effect of varying linker length on the transglycosylation activity of CelE was tested by reacting different construct with pNP-Cellobiose at 60° C. for 4 hours.

Figure 7A:
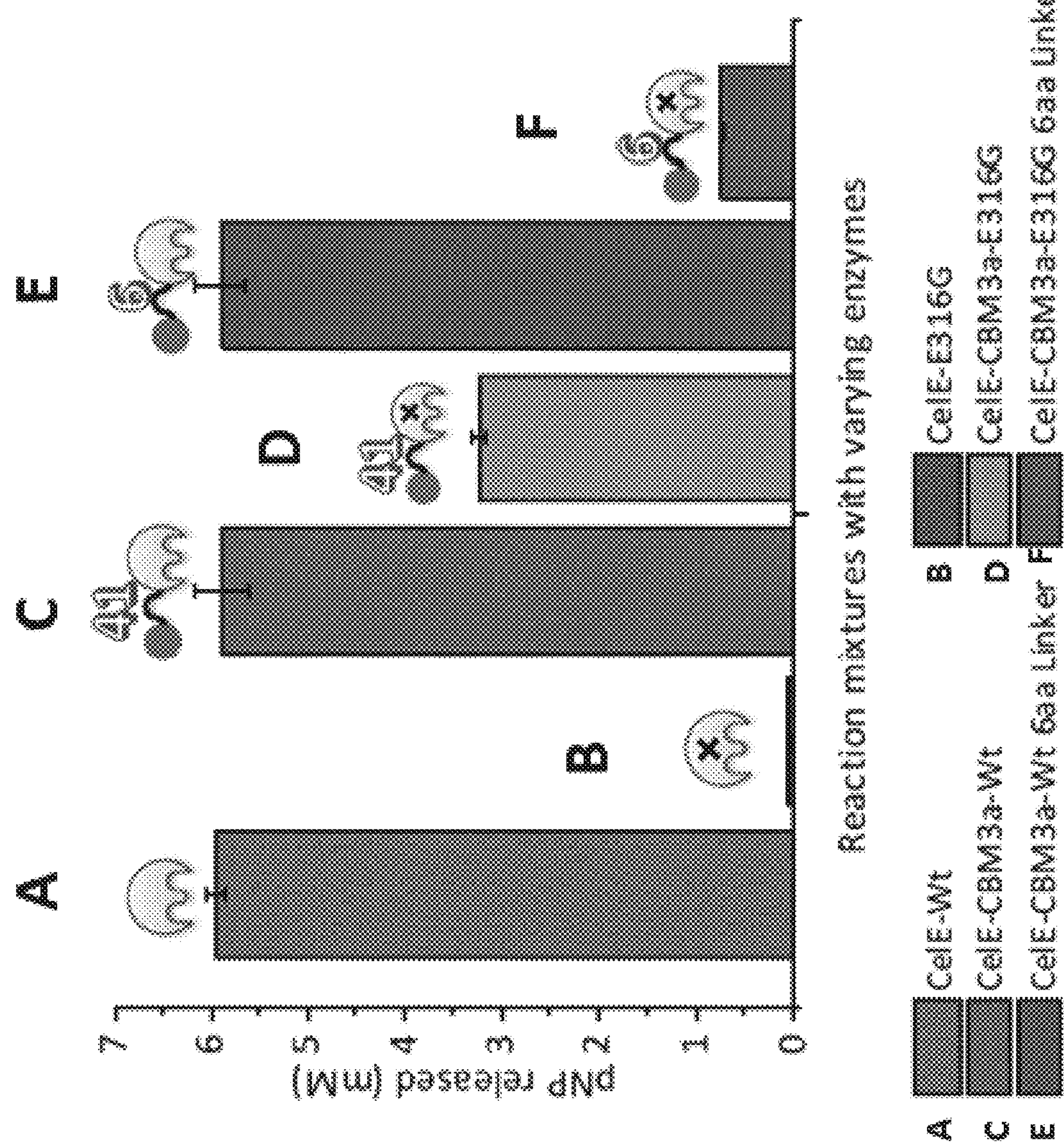
FIG. 7A illustrates that linker length affects the efficiency of glycan polymer synthesis.
Figure 7B:
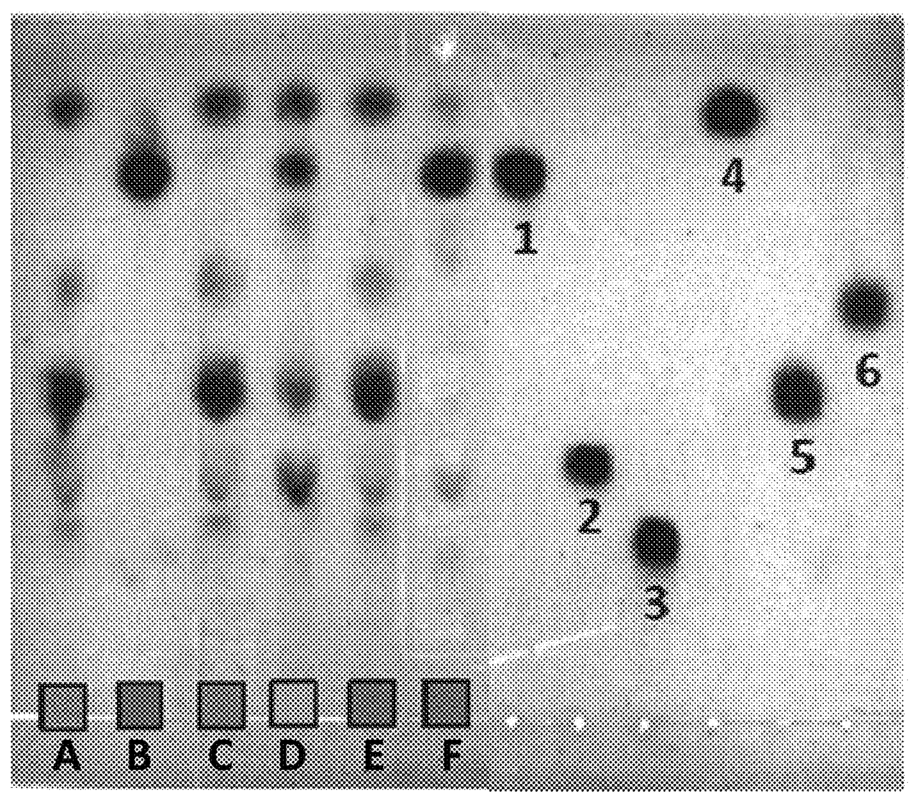
FIG. 7B illustrates that TLC analysis of the cellobiose polymer synthesis reaction mixture shows that reaction catalyzed by CelE-CBM3a-E316G construct having a 41 amino acid linker yields significantly more polymerization product compared to the reaction catalyzed by CelE-CBM3a-E316G construct having a 6 amino acid linker.

FIGS. 7*a* and 7*b* show that shortening the length of the linker domain from ~40 amino acids to 6 amino acids for CelE-E316G-CBM3a results in a significant drop in transglycosylation reaction. These results provide supporting evidence that the CBM domain is interacting with the mutant catalytic domain to increase biosynthesis capability of the enzyme construct.

Enumerated Embodiments

The following exemplary embodiments are provided, the numbering of which is not to be construed as designating levels of importance.

Embodiment 1 provides a construct comprising a Glycoside Hydrolase (GH) catalytic domain (CD), which is conjugated to a carbohydrate binding module 3a (CBM3a), wherein the CD is mutated with respect to its wild-type form so that the mutated CD is capable of catalyzing glycan polymer synthesis.

Embodiment 2 provides the construct of Embodiment 1, wherein the wild-type CD is capable of hydrolyzing at least one substrate selected from the group consisting of cellulose, mannan, galactomannan, and xylan.

Embodiment 3 provides the construct of any of Embodiments 1-2, wherein the GH comprises at least selected from the group consisting of GH5, GH7, GH8, and GH12.

Embodiment 4 provides the construct of any of Embodiments 1-3, wherein the GH is GH5 and the CD comprises a E316G mutation.

Embodiment 5 provides the construct of any of Embodiments 1-3, wherein the GH is GH5 and the CD comprises a E193A mutation.

Embodiment 6 provides the construct of any of Embodiments 1-3, wherein the CD is conjugated to the CBM3a through a linker.

Embodiment 7 provides the construct of any of Embodiments 1-6, wherein the linker is peptidic.

Embodiment 8 provides the construct of any of Embodiments 1-7, wherein the linker comprises about 7-200 amino acids.

Embodiment 9 provides the construct of any of Embodiments 1-8, wherein the linker comprises about 15-41 amino acids.

Embodiment 10 provides the construct of any of Embodiments 1-9, wherein the N-terminus of the CD is conjugated to the C-terminus of the CBM3a through the linker.

Embodiment 11 provides the construct of any of Embodiments 1-9, wherein the C-terminus of the CD is conjugated to the N-terminus of the CBM3a through the linker.

Embodiment 12 provides the construct of any of Embodiments 1-11, which has higher glycan polymer synthesis activity than the mutated CD when not conjugated to the CBM3a.

Embodiment 13 provides the construct of any of Embodiments 1-12, which catalytic activity is at least 2-fold higher than the mutated CD when not conjugated to the CBM3a.

Embodiment 14 provides the construct of any of Embodiments 1-13, which comprises a CBM3a-linker polypeptide encoded by the nucleotide sequence of any of SEQ ID NOs. 1, 3, 5, 7, 9, 11, 13.

Embodiment 15 provides the construct of any of Embodiments 1-14, which comprises a CBM3a-linker polypeptide with at least 70% homology with the amino acid sequence of any of SEQ ID NOs. 2, 4, 6, 8, 10, 12, 14.

Embodiment 16 provides the construct of any of Embodiments 1-15, which comprises a polypeptide that is encoded by the nucleotide sequence of any of SEQ ID NOs. 1, 3, 5, 7, 9, 11, 13, 15, 17, 19, 21, 23, 25, 27.

Embodiment 17 provides the construct of any of Embodiments 1-16, which comprises a polypeptide with at least 70% homology with the amino acid sequence of any of SEQ ID NOs. 2, 4, 6, 8, 10, 12, 14, 16, 18, 20, 22, 24, 26, 28, 29, 30.

Embodiment 18 provides a method for promoting glycan polymer synthesis, the method comprising contacting a glycosyl donor substrate with an effective amount of the construct of any of Embodiments 1-17.

Embodiment 19 provides the method of Embodiment 18, wherein the substrate includes at least one selected from the group consisting of cellobiose, glucose, xylose, and mannose.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A construct comprising a Glycoside Hydrolase (GH) catalytic domain (CD), wherein the GH CD is conjugated to a carbohydrate binding module (CBM) selected from carbohydrate binding module 1 (CBM1), carbohydrate binding module 3a (CBM3a), and carbohydrate binding module 17 (CBM17), wherein the GH CD comprises amino acid residues 38-377 of SEQ ID NO. 6, with the proviso that in the GH CD at least one of the Glu amino acid residues at positions 180 and 303 of SEQ ID NO. 6 is mutated to an independently selected non-nucleophilic amino acid.

2. The construct of claim 1, wherein the GH CD polypeptide comprising amino acid residues 38-377 of SEQ ID NO. 6 is capable of hydrolyzing at least one substrate selected from the group consisting of cellulose, mannan, galactomannan, and xylan.

3. The construct of claim 1, wherein at least one applies:

(a) the carbohydrate binding module 1 (CBM1) comprises amino acid residues 420-459 of SEQ ID NO. 2;

(b) the carbohydrate binding module 3a (CBM3a) comprises amino acid residues 420-578 of SEQ ID NO. 6;

(c) the carbohydrate binding module 17 (CBM17) comprises amino acid residues 420-601 of SEQ ID NO. 4.

4. The construct of claim 1, wherein the Glu amino acid residue at position 303 of SEQ ID NO. 6 is mutated to Gly or Ala.

5. The construct of claim 1, wherein the Glu amino acid residue at position 180 of SEQ ID NO. 6 is mutated to Gly or Ala.

6. The construct of claim 1, wherein the GH CD is conjugated to the CBM through a linker.

7. The construct of claim 6, wherein the linker is peptidic.

8. The construct of claim 7, wherein the linker comprises about 7-200 amino acids.

9. The construct of claim 7, wherein the linker comprises about 15-41 amino acids.

10. The construct of claim 1, wherein the N-terminus of the GH CD is conjugated to the C-terminus of the CBM through the linker.

11. The construct of claim 1, wherein the C-terminus of the GH CD is conjugated to the N-terminus of the CBM through the linker.

12. The construct of claim 1, which has higher glycan polymer synthesis activity than the mutated GH CD when not conjugated to the CBM.

13. The construct of claim 12, which catalytic activity is at least 2-fold higher than the mutated GH CD when not conjugated to the CBM.

14. The construct of claim 1, which is encoded by the nucleotide sequence of any of SEQ ID NOs. 15, 17, 19, 21, 23, 25, and 27.

15. The construct of claim 1, which comprises the amino acid sequence of any of SEQ ID NOs. 16, 18, 20, 22, 24, 26, and 28.

16. A method for producing a glycan polymer, the method comprising contacting a glycosyl donor substrate with an effective amount of the construct of claim 1.

17. The method of claim 16, wherein the substrate includes at least one selected from the group consisting of cellobiose, glucose, xylose, and mannose.

* * * * *